(12) United States Patent
Mantripragada et al.

(10) Patent No.: US 10,213,487 B2
(45) Date of Patent: Feb. 26, 2019

(54) NASAL POWDER FORMULATION FOR TREATMENT OF HYPOGLYCEMIA

(71) Applicant: Eli Lilly and Company, Indianapolis, IN (US)

(72) Inventors: Sankaram Mantripragada, Windsor, CO (US); Claude A. Piche, Verdun (CA); Jo Jan Filip Van Betsbrugge, Laval (CA)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/545,332

(22) PCT Filed: Feb. 16, 2016

(86) PCT No.: PCT/US2016/018003
§ 371 (c)(1),
(2) Date: Jul. 21, 2017

(87) PCT Pub. No.: WO2016/133863
PCT Pub. Date: Aug. 25, 2016

(65) Prior Publication Data
US 2018/0000904 A1 Jan. 4, 2018

Related U.S. Application Data

(60) Provisional application No. 62/117,031, filed on Feb. 17, 2015.

(51) Int. Cl.
*A61K 38/26* (2006.01)
*A61K 9/00* (2006.01)
*A61K 9/14* (2006.01)
*A61K 31/724* (2006.01)
*A61K 47/12* (2006.01)
*A61K 47/24* (2006.01)
*A61M 15/00* (2006.01)
*A61M 15/08* (2006.01)

(52) U.S. Cl.
CPC ............ *A61K 38/26* (2013.01); *A61K 9/0043* (2013.01); *A61K 9/145* (2013.01); *A61K 9/146* (2013.01); *A61K 31/724* (2013.01); *A61K 47/12* (2013.01); *A61K 47/24* (2013.01); *A61M 15/0065* (2013.01); *A61M 15/08* (2013.01); *A61M 2202/064* (2013.01)

(58) Field of Classification Search
None
See application file for complete search history.

(56) References Cited

U.S. PATENT DOCUMENTS

| 5,179,079 A | 1/1993 | Hansen et al. |
| 2006/0074025 A1 | 4/2006 | Nastech |
| 2011/0237510 A1 | 9/2011 | Biodel |
| 2013/0053310 A1* | 2/2013 | Lau .................. C07K 14/605 514/6.8 |

FOREIGN PATENT DOCUMENTS

| WO | WO 92/16196 | * 10/1992 |
| WO | WO9216196 | 10/1992 |

OTHER PUBLICATIONS

Sakr ((1996). Nasal administration of glucagon combined with dimethyl-p-cyclodextrin: comparison of pharmacokinetics and pharmacodynamics of spray and powder formulations. International journal of pharmaceutics, 732(1-2), 189-194).*
Pontiroli, A. E. (2014). Intranasal glucagon: a promising approach for treatment of severe hypoglycemia. *Journal of diabetes science and technology*, 9(1), 38-43.
Abe K, Irie T, Uekama K. Enhanced nasal delivery of luteinizing hormone releasing hormone agonist buserelin by oleic acid solubilized and stabilized in hydroxypropyl-beta-cyclodextrin. *Chem Pharm Bull* (Tokyo). 1995;43:2232-2237.
Sakr, F. M. (1996). Nasal administration of glucagon combined with dimethyl-β-cyclodextrin: comparison of pharmacokinetics and pharmacodynamics of spray and powder formulations. *International journal of pharmaceutics*, 132(1-2), 189-194.

* cited by examiner

*Primary Examiner* — Maury A Audet
(74) *Attorney, Agent, or Firm* — Jennifer K Gregory

(57) ABSTRACT

The present invention provides a powder formulation containing glucagon or a glucagon analog for nasal administration, useful in the treatment of hypoglycemia, and in particular the treatment of severe hypoglycemia. The present invention also provides a method of making this powder formulation, and to devices and methods for using the powder formulation.

19 Claims, 12 Drawing Sheets
Specification includes a Sequence Listing.

NASAL POWDER FORMULATION FOR TREATMENT OF HYPOGLYCEMIA

FIELD OF THE INVENTION

This application relates to a powder formulation containing glucagon or a glucagon analog for nasal administration, useful in the treatment of hypoglycemia, and in particular the treatment of severe hypoglycemia. The application further relates to a method of making this powder formulation, and to devices and methods for using the powder formulation.

BACKGROUND OF THE INVENTION

Diabetes has reached epidemic proportions in much of the western world and is a serious and growing public health concern in many developing economies. Globally, there are approximately 285 million people with diabetes and that number is expected to reach 438 million by 2030 (IDF Diabetes Atlas, 2009.)

Diabetes complications are usually associated with chronically elevated blood glucose levels (hyperglycemia), which result in heart, kidney and eye diseases, amputations and neurological impairment. Unfortunately, there are very real and serious complications associated with use of medications used to treat the diabetes-related hyperglycemia. One of the most common complications of treatments used to reduce blood sugar levels is hypoglycemia (low blood sugar), most frequently seen in patients being treated with insulin (i.e., all persons with type 1 diabetes and approximately 30% of patients with type 2 diabetes) but also in patients with type 2 diabetes receiving sulfonylurea treatment. Indeed, if it was not for the barrier of hypoglycemia, people with diabetes could probably have normal blood glucose levels and thus avoid the complications associated with hyperglycemia (Cryer, 2002).

Depending on the severity of the episode, hypoglycemia causes a wide range of physical problems ranging from weakness, dizziness, sweating, chills and hunger to more serious symptoms including blurred vision, behavior change, seizures, coma and even death. In addition to the physical effects of hypoglycemia, there are significant psychological effects including embarrassment, fear of another episode, high levels of anxiety and low levels of overall happiness that adversely affect glucose control and quality of life (Deary, 2008).

Severe hypoglycemia in a conscious person should be treated by the oral ingestion of carbohydrate, preferably as glucose tablets or equivalent. For severe hypoglycemia in an unconscious individual outside of the hospital setting, the recommended treatment is 1 mg of glucagon by intramuscular (IM) or subcutaneous (SC) injection. For severe hypoglycemia in an unconscious individual in the presence of professional medical assistance and intravenous access, intravenous dextrose is recommended. In all cases, once the hypoglycemia has been reversed, the patient should be given access to oral carbohydrates to fully recover and prevent repeated hypoglycemia.

Glucagon, a highly effective treatment for severe hypoglycemia both outside and within the hospital setting, is currently available only as a powder that must be mixed with a diluent immediately prior to administration by injection. Although this is a procedure that would be relatively easy for people with diabetes who inject insulin, they are not treating themselves because, by definition, severe hypoglycemia is a hypoglycemic episode in which the patient requires third party assistance (Cryer, 2009). For any non-medical person who is confronted with an emergency situation in which a patient with diabetes is in a hypoglycemic coma or suffering hypoglycemia-related convulsions, reconstitution and injection of the current injectable glucagon is a complex and daunting procedure that is fraught with potential for errors.

Indeed, Australian researchers have published a study in which parents of children and adolescents with diabetes used one of the currently available glucagon kits (GlucoGen Hypokit, Novo Nordisk) in a simulated emergency situation (Harris et al, 2001). Each parent was asked to pretend it was 3:00 am and their child was unconscious. They were then given an unopened emergency glucagon kit and asked to administer the medication in a wrapped piece of meat to simulate a thigh. A small of group of 11 diabetes health professionals (five endocrinologists and six diabetes educators) served as surrogate control.

Of the 136 parents who participated in the study, 106 were parents of teenagers with a mean duration of diabetes of 4.7 years and 30 were parents of younger children with a mean duration of diabetes of 2.4 years. Over 90% reported having been previously trained on use of glucagon. Fully 69% of these parents experienced difficulties handling the current glucagon emergency kit. Difficulties included difficulty in opening the pack, removal of the needle sheath, mixing of the ingredients and bending of needles. On average, these parents required 2 minutes and 30 seconds to complete the procedure (range 30 seconds to >12 minutes). In addition, 6% aborted the injection entirely and 4% of the participants injected only air or only diluent. In contrast, diabetes professionals performed the procedure in 1 minute and 17 seconds (range 1-1.75 minutes). The number of errors observed in this sample of parents is disconcerting especially in light of the fact that this was a timed simulation and not a true emergency.

Difficulties associated with use of the glucagon emergency kit are corroborated in a recent report from the Institute for Safe Medication Practices (ISMP) Canada (ISMP Canada Safety Bulletin, 2010). The ISMP report of September 2010 documents three separate incidents in which the diluent was administered on its own, without the glucagon powder having been reconstituted with the diluent before administration. This resulted in complete failure to deliver the intended dose of glucagon to individuals experiencing a severe hypoglycemic crisis and, according to the report, resulted in patient harm in one of the cases.

A telephone survey was conducted with 102 patients with type 1 diabetes to ascertain their opinions on the currently available glucagon emergency kits (Yanai, 1997). Most patients (67%) stated they would prefer an intranasally administered glucagon were it available and fully 82% of these patients assumed family members, teachers and colleagues would prefer to administer emergency therapy by the intranasal route. Likewise, amongst emergency care professionals who are frequently the first to be called to treat a patient suffering from an episode of severe hypoglycemia, there is significant concern regarding the injected route of administration. Inherent in using sharps, there is the very real risk of accidental blood exposure and needlestick and the associated potential for contracting life-threatening infectious diseases (Leiss J 2006). Within this context, some emergency professionals are actively seeking noninvasive routes of administration, including intranasal, as a means to enhance emergency patient care, increase patient and caregiver safety while increasing the pool of care providers who can effectively respond to the emergency (Curran, 2007).

These considerations make it clear that the present approach to the administration of glucagon in emergency situations is lacking, and that there exists a real need for alternative approaches for delivering glucagon to treat severe hypoglycemia.

Various approaches to delivery of glucagon via intranasal administration have been proposed but they have not resulted in the availability of an approved alternative to injected glucagon. In general, these approaches can be divided into two groups, those that use administer a liquid formulation, and those that use some type of dry formulation.

Within the liquid formulations group, the compositions used in Pontiroli (1983), Pontiroli (1985), Freychet (1988), Pontiroli (1989), Pontiroli (1993) and Pacchioni (1995) were all formulations that needed to be sprayed into the nose. More recently, Sibley et al., 2013, reported successful use of what was intended to be injectable glucagon by spraying the reconstituted glucagon solution intranasally in a patient in the out-of-hospital environment.

Because glucagon is not stable in the liquid state, the liquid compositions used in these studies needed to be reconstituted immediately prior to use and are therefore not ideal for emergency use in treating severe hypoglycemia. Further, in many of these studies, patients needed to take a deep breath immediately after dosing with these compositions. Since patients with severe hypoglycemia are frequently unconscious or even comatose, they cannot be asked to take a deep breath. As such, these compositions are not ideal for intranasal delivery for treatment of severe hypoglycemia, and do not overcome the challenges of injectable formulations that involve use of a needle by non-medical professionals and need to be prepared prior to use.

Within the second group, U.S. Pat. No. 5,059,587 discloses powders for nasal administration of physiologically active peptides, including glucagon. These powders include a water-soluble organic acid as an absorption promoter.

Jorgensen et al. 1991 disclosed a "powdery formulation of glucagon for nasal delivery." This formulation is disclosed as containing glucagon, didecyl phosphatidylcholine (DDPC) and α-cyclodextrin (α-CD), and is reported as providing a dosage dependent response with respect to increases in plasma glucose and plasma glucagon. No compositional amounts or method of making the formulation are disclosed in this reference.

The Jorgensen 1991 formulation or HypoGon® Nasal (NovoNordisk) is identified as the material used in several subsequent studies, and in one of these reports the formulation is said to have a composition of glucagon:DDPC: α-CD in a 5:10:85 ratio by weight. In these studies, intranasal administration to adults of the Jorgensen 1991 powder formulation is reported to show an increase in plasma glucose concentration in adults with hypoglycemia. In these studies, glucose levels increased after dosing to reach a plateau at about 30 minutes after dosing. In contrast, treatment with injected glucagon in these studies resulted in glucose levels that continued to increase from the time of administration for up to at least 90 minutes (Hvidberg, 1994; Rosenfalck, 1992). Intranasal administration to children with hypoglycemia of the Jorgensen 1991 powder formulation is reported to increase plasma glucose concentration soon after dosing to peak levels 25-30 minutes post-dosing after which glucose levels decreased. In contrast, treatment of children with injected glucagon resulted in plasma glucose levels that continued to rise for at least 45 minutes (Stenninger, 1993).

Sakr, 1996 reports a comparison of spray and powder formulations containing glucagon and dimethyl-β-cyclodextrin (DMβCD). Nasal spray was prepared by dissolving commercial glucagon in the "manufacturer's solvent" containing 2 or 5% w/v DMβCD. Powders were obtained by freeze drying of the spray solutions.

Teshima et al (2002) found that a maximum plasma glucose increase of 1.56 mmol/L (28.08 mg/dL) in healthy volunteers upon intranasal administration of a powder containing glucagon and microcrystalline cellulose at a ratio of 1:69. They also reported that the powder form is stable at 5 and 25° C. for at least 84 days. For an intranasal product in patients with insulin-induced hypoglycemia, an increase of only 1.5 mmol/L may be inadequate to bring the patient back to normal blood glucose levels. In addition, the volume of powder (i.e., 70 mg for a 1:69 ratio formulation) is considerable and may be excessive for use with available devices.

Matilainen et al (2008, 2009) investigated the solid-state stability and dissolution of glucagon/γ-CD and glucagon/lactose powders at an increased temperature and/or humidity for up to 39 weeks, with the solid state stability of the glucagon/γ-CD powder being better. The powder was not used for intranasal administration.

Endo et al (2005) reported that the use of erythritol as both an excipient and a carrier in a dry-powder inhaler of glucagon for pulmonary administration. The powder was formulated by mixing micronized glucagon particles and excipients with larger carrier particles. To achieve alveolar deposition for subsequent systemic absorption, a dry powder inhalant (DPI) of glucagon was size-reduced to a mass median diameter between 1 and 6 micron, as measured by laser diffraction analysis.

Onoue et al (2009) reported that addition of citric acid in glucagon dry-powder inhaler for pulmonary inhalation improved the dissolution behavior, and did not impair the solid-state stability. Intratracheal administration of glucagon dry-powder inhaler (50 μg/kg in rats) containing citric acid led to 2.9-fold more potent hyperglycemic effect in rats, as compared to inhaled glucagon without citric acid. Both the Endo (2005) and Onoue (2009) disclosures present pulmonary delivery of glucagon. As patients with severe hypoglycemia may be unconscious or severely disoriented, they cannot be expected to breathe deeply to assure pulmonary delivery. As such, pulmonary delivery of glucagon is not appropriate for treatment of severe hypoglycemia.

Notwithstanding these efforts, no current product is available to patients that utilizes a nasal powder to administer glucagon for the treatment of severe hypoglycemia.

It is an object of the present invention to provide such a nasal powder formulation.

SUMMARY OF THE INVENTION

In accordance with a first aspect of the present invention, a powder formulation of glucagon or a glucagon analog is provided. This powder composition comprises glucagon or a glucagon analog, a cyclodextrin, and a phospholipid surfactant, and is formulated such that at least a portion of the powder is present in a phase characterized by an XRPD mesopeak as determined by x-ray powder diffraction. In further specific embodiments, the powder composition consists of:
(a) 5 to 15 wt % glucagon or glucagon analog;
(b) 5 to 51 wt % of phospholipid surfactant;
(c) 44 to 90 wt % of cyclodextrin and (d) optionally, up to 10 wt % of a low molecular weight organic acid, or a pharmaceutically acceptable water soluble salt of ester thereof.

In accordance with a second aspect of the invention, a nasal applicator for a powder formulation is provided. The applicator includes a powder formulation reservoir, and a powder formulation in accordance with the invention contained within the reservoir In accordance with a third aspect of the invention, a method for making the powder formulation of the invention is provided. This method comprises the steps of:
(a) forming a first mixture of the glucagon and the surfactant in an aqueous carrier, wherein the surfactant is present at a concentration greater than or equal to the critical micelle concentration;
(b) adding the cyclodextrin to the first mixture to form a second mixture;
(c) drying the second mixture to form a solid formulation; and
(d) processing the solid formulation to produce a uniform powder, said uniform powder including at least a portion of the powder in a phase characterized by an XRPD mesopeak.
In specific embodiments, the drying of the second mixture may be carried out by freeze drying or spray drying the second mixture.

DETAILED DESCRIPTION OF THE INVENTION

Figure 1:
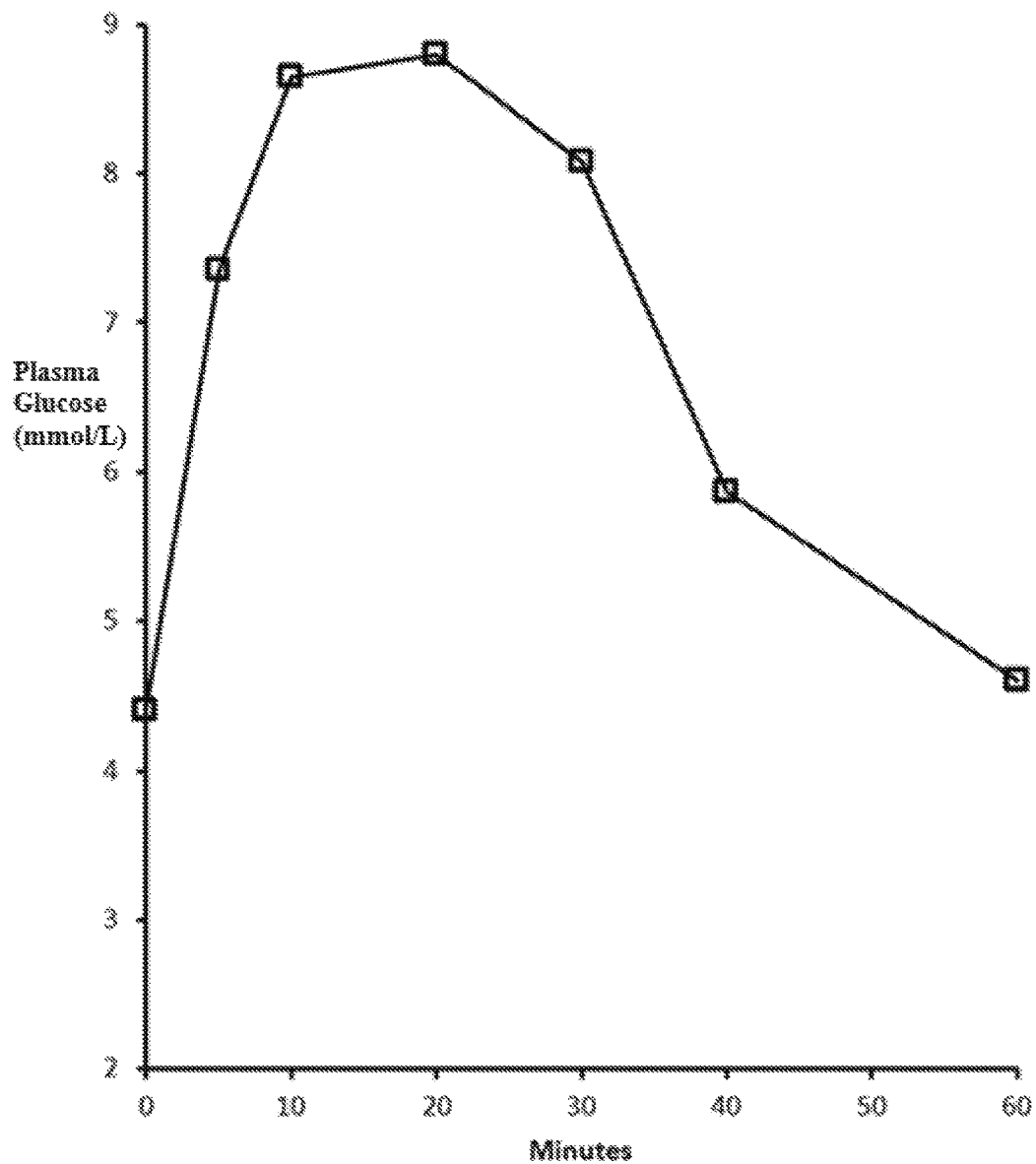
FIG. 1: Plasma glucose concentration in mmol/L over time upon intranasal administration to dogs at a 1 mg dose of glucagon via a powder formulation with a glucagon:DPC: ß-CD weight ratio of 10:10:80.

Some of the desired attributes for an intranasal powder formulation with commercial potential are listed below.
Uniform dose deliverability by a device for intranasal administration
Absence of a significant fraction of small particles to preclude inadvertent administration to the lungs
Adequate drug content to provide the total dose of drug required to achieve therapeutic effect as a single dose into a single nostril
Adequate drug content to deliver the total dose in a few tens of milligrams, or the maximum allowed by the delivery device
Adequate drug content and absorption characteristics to be effective despite the presence of nasal congestion that may be associated with allergies or common cold
Stability during storage under ambient conditions for an extended period of time, preferably at least 18 months
Good safety and tolerability profile Previous attempts at developing an intranasal powder formulation fall short in one or several of the desired attributes.

Compositions described in this invention are designed to meet some and preferably all of these desired attributes in compositions having three required components: glucagon or a glucagon analog, a cyclodextrin, and a phospholipid surfactant.

Glucagon and Glucagon Analogs

As used in the specification and claims of this application, "glucagon" refers to a polypeptide of the sequence (SEQ ID NO: 1)
His-Ser-Gln-Gly-Thr-Phe-Thr-Ser-Asp-Tyr-Ser-Lys- Tyr-Leu-Asp-Ser-Arg-Arg-Ala-Gln-Asp-Phe-Val-Gln- Trp-Leu-Met-Asn-Thr.

The glucagon may be chemically synthesized, produced by recombinant DNA technology or extracted from natural sources. The term "glucagon analog" refers to variants of this sequence that retain the ability to stimulate increase in blood glucose in vivo but which may offer benefits for pharmaceutical uses such as greater activity, greater solubility or greater stability.

Examples of glucagon analogs in which one amino acid of the natural sequence is replaced with an alanine as well as analogs with multiple substitutions are disclosed in Chabenne et al., (2014), which is incorporated herein by reference. An exemplary analog in which three amino acids are modified to result in a glucagon analog with enhanced biological activity is [Lys$^{17,18,}$ Glu$^{21}$] glucagon. Zealand Pharma has disclosed a multitude of glucagon analogs for example in US Patent Publications 20140080757, 2014001733, 20130316941, 20130157935, 20130157929, 20120178670, 20110293586, 20110286982, 20110286981, and 20100204105 which are incorporated herein by reference. These analogs are reported to have greater binding affinity for the GLP receptor than the glucagon receptor, but nonetheless retain the activity of glucagon. Zealand Pharma has also commenced clinical trials of a glucagon analog for treatment of hypoglycemia designated as ZP4207. US Patent Publication 20130053310, which is incorporated herein by reference, discloses other glucagon analogs useful in treatment of hypoglycemia.

Phospholipid Surfactants

Phospholipids are ubiquitous components of biological membranes that are part of cells and tissues in the human body, including the nasal mucosa. The most prevalent phospholipid surfactants in cell are phosphatidylcholines and phosphocholines (PC), although phosphatidylglycerols (PG) are significant components of biological membranes.

PCs and PGs may be used in the formulations of the invention. Lysophospholipids derived from a diacyl PC or PG by removal one of the acyl groups may also be used. Preferred phospholipids are soluble in water or acidified water, although a pharmaceutically acceptable cosolvent such as ethanol, dimethylsullfoxide or N-methylpyrrolidone could be used if needed to enhance phospholipid solubility.

In accordance with the present invention, exemplary phospolipid surfactants that may be employed in the powder formulation are dodecylphosphocholine (DPC), 1,2-didecyl-sn-glycero-3-phosphocholine (DDPC or "didecylphosphatidylcholine"), 1-didecanoyl-sn-glycero-3-phosphocholine (LLPC or "lysolauroylphosphatidylcholine"), 1,2-dioctanoyl-sn-glycero-3-phosphocholine (D8PC or "dioctanoyl-phosphatidylcholine") and 1,2-dilauroyl-sn-glycero-3-phospho(1'-rac-glycerol) (DLPG or "dilauroylphosphatidylglycerol").

Preferred phospholipid surfactants are those that form micelles, rather than bilayers at the concentration used during manufacture of the powder formulation. This includes DPC, DDPC, LLPC, and D8PC, but not DLPG.

In general, the formation of micelles as opposed to bilayers can be predicted based on the structure of the phospholipid surfactants, which are made of two or three parts: a phosphorous-containing choline or glycerol headgroup, an optional glycerol backbone and one or two acyl chains. The length of the acyl chain and number of acyl chains per molecule are important in determining whether a certain phospholipid forms a micelle or a bilayer. Where only one acyl chain is present, as in DPC and LLPC which have 12 carbons in their single acyl chain, micelles are likely to be formed as opposed to bilayers provided the length of the acyl chain is less than 14. Diacyl phospholipids contain two acyl chains per molecule. When the chain length of each chain is less than 12, they tend to form micelles. DLPG, DDPC and D8PC are diacyl phospholipids. DLPG contains 12 carbons per acyl chain and forms bilayers. DDPC contains 10 carbons per acyl chain. It forms either bilayers or micelles depending on the concentration (Marsh, 1990). D8PC contains 8 carbons per acyl chain, and mostly forms micelles.

In specific embodiments of the invention, the formulation contains a single type of phospholipid surfactant. In other embodiments, the phospholipid surfactant component of the formulation can be made up from mixtures of phospholipid surfactants, including for example, a combination of any two, three or four of the surfactants identified above.

Cyclodextrins

Cyclodextrins as a class are composed of 5 or more α-D-glucopyranoside units linked 1->4, as in amylose (starch). As used in this application, however, the term "cyclodextrins" refers to the more common and typical cyclodextrins containing six, seven or eight glucose residues in the ring creating a cone shape, namely:

α (alpha)-cyclodextrin: 6-membered sugar ring molecule
β (beta)-cyclodextrin: 7-membered sugar ring molecule
γ (gamma)-cyclodextrin: 8-membered sugar ring molecule α-CD was used in the powder formulation (HypoGon® Nasal) by Novo Nordisk in clinical trials (Stenniger and Aman, 1993; Rosenfalck, 1992). The aqueous solubility of α-CD is reported to be about 5 wt %.

Two other cyclodextrins, one with aqueous solubility less than that of α-CD (ß-CD, 1.85 wt %) and another with a higher aqueous solubility than α-CD (HP-ß-CD) are also suitable for use in the compositions of the invention, as is γ (gamma)-cyclodextrin which is freely soluble in water.

Cyclodextrins in the compositions of the invention act as a filler, and also adhere to the nasal mucosal surface and aid in the absorption of glucagon. Upon delivery to the nostril, the major ingredient (90% to 70% by weight) namely, the cyclodextrin helps the powder adhere to the mucosal surface. The less soluble the cyclodextrin is, the longer the powder is expected to be physically muco-adhesive. Based on the solubility properties of cyclodextrins, the muco-adhesiveness is expected to decrease in the order ß-CD>α-CD>HP-ß-CD. Because of this, the most preferred filler is ß-CD.

The cyclodextrins of the invention may be used individually, or as mixtures of any two or more cyclodextrins.

Powder Formulation

The powder formulation of the invention contains the three ingredients, the glucagon or glucagon analog, the phospholipid surfactant and the cyclodextrin in amounts that are effective to provide a therapeutic amount of glucagon or glucagon analog in an amount of powder that can be administered in a single dose in a single nostril. In specific embodiments, the powder formulation consists of:

(a) 5 to 15 wt % glucagon or a glucagon analog;
(b) 5 to 51 wt % of phospholipid surfactant;
(c) 44 to 90 wt % of cyclodextrin and
(d) optionally, up to 10 wt % of a low molecular weight organic acid, or a pharmaceutically acceptable water soluble salt of ester thereof.

As reflected in the examples below, powder formulations of this type have excellent properties when used to administer glucagon intranasally, yet a similar set of ingredients in the Jorgensen 1991/Rosenfalck 1992/HypoGon® Nasal product did not provide comparable results and was apparently abandoned following initial testing in human subjects.

Based on the various descriptions in the art, it is believed the Jorgensen 1991/Rosenfalck 1992/HypoGon® Nasal product contained glucagon, DDPC and alpha-CD in a weight ratio of 5:10:85. No information is provided about how these ingredients were combined. Thus, a direct comparison of this formulation with the formulation of the invention is not possible. However, the available data for each formulation illustrates the fact that the formulations are different. Importantly, the formulation described in Jorgensen 1991/Rosenfalck 1992 was administered in a divided dose with one half a dose administered in each nostril. While this may be relatively easily performed in a clinical research setting, under practical use conditions, this significantly complicates rescue treatment for non-medical caregivers in treating an episode of severe hypoglycemia, as it would require administering two doses of rescue medication. They also report sneezing in 50% of treated patients, a rate much higher than that observed (less than 2%) with the formulation described in this invention.

Intranasal administration to adults of the Jorgensen 1991 powder formulation is reported to show an increase in plasma glucose concentration in adults with hypoglycemia. In healthy adults with insulin induced hypoglycemia, glucose levels increased after dosing to reach a plateau at about 45 minutes after dosing. In contrast, treatment with injected glucagon in this study resulted in glucose levels that continued to increase from the time of administration for up to at least 90 minutes (Hvidberg, 1994). In another study conducted with adults with type 1 diabetes and insulin-induced hypoglycemia, glucose levels increased after dosing to reach a plateau at about 30 minutes after intranasal dosing, compared to at least 90 minutes for injected glucagon (Rosenfalck, 1992).

Figure 7:
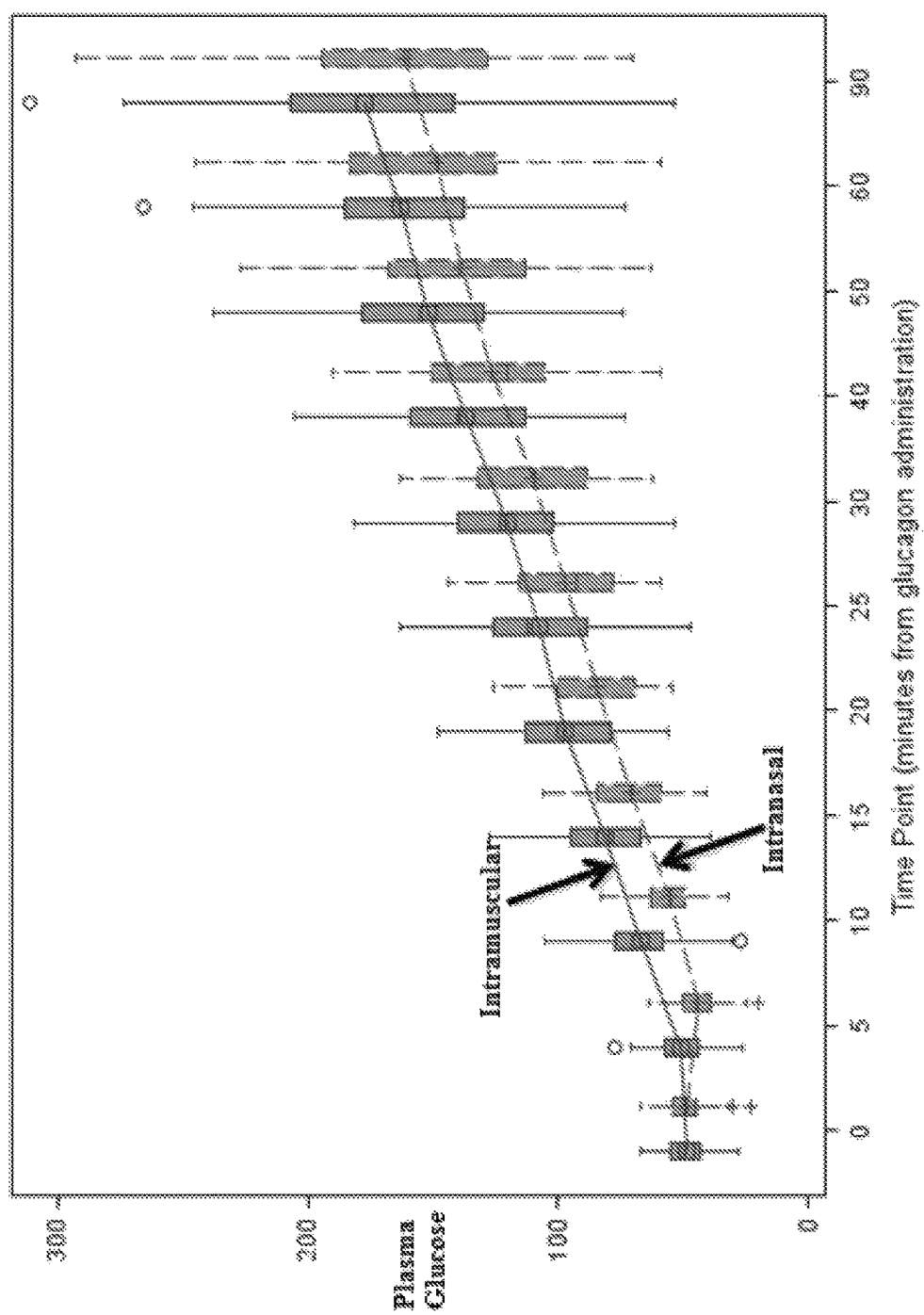
FIG. 7: Average plasma glucose concentrations in adults with type 1 diabetes and insulin-induced hypoglycemia treated with intranasal and injected glucagon.

In contrast to the glucose profile observed with the Jorgensen 1991/Rosenfalck 1992 formulation, data generated with the powder formulation described in this invention show that plasma glucose concentrations continue to rise for at least 90 minutes after dosing (FIG. 7, bottom line). As shown, this is comparable to the result obtained with intramuscular glucagon over the same time period (FIG. 7, top line).

Figure 8A:
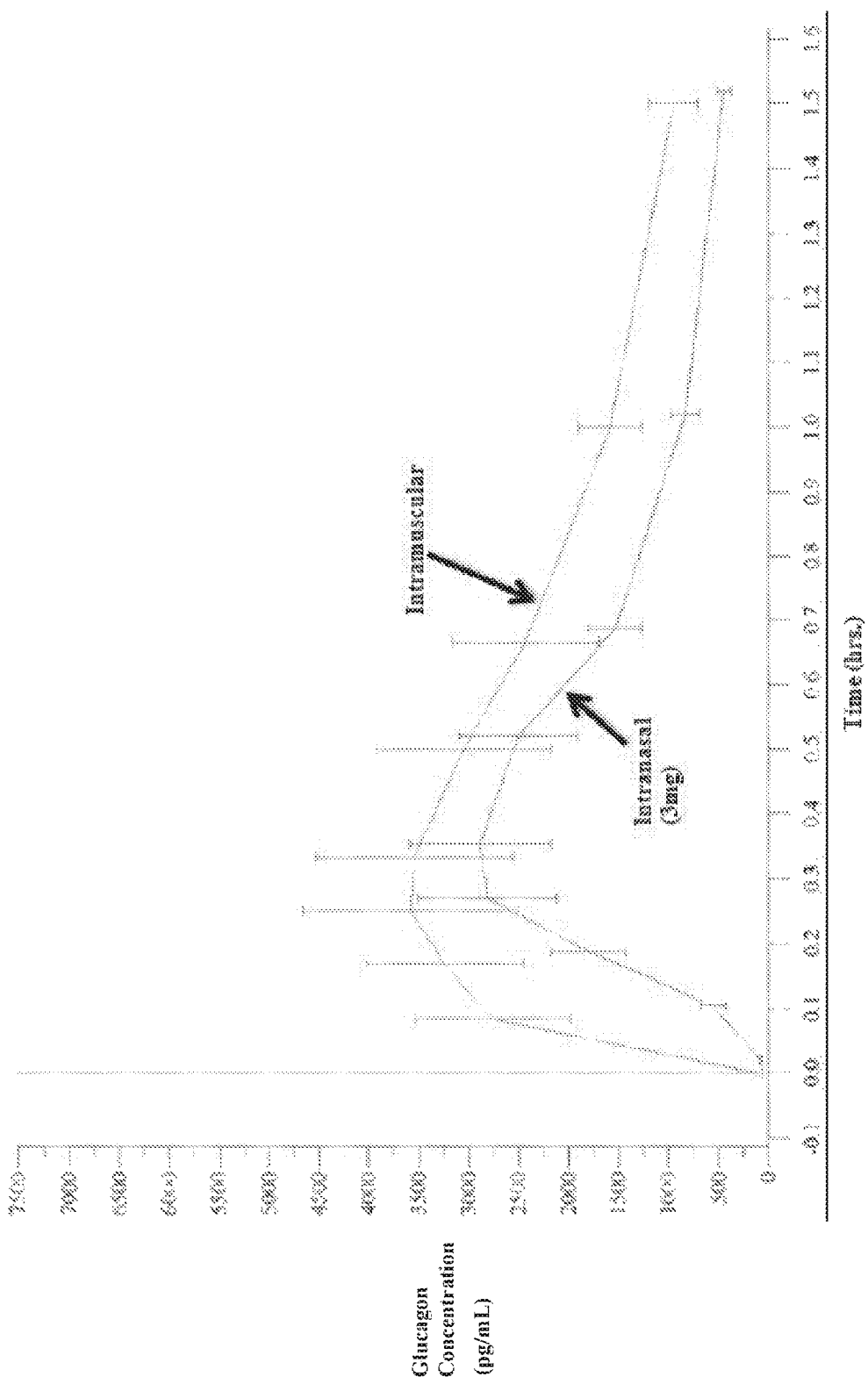
FIG. 8A: Average plasma glucagon concentrations in children, ages 12-17, with type 1 diabetes treated with intranasal and injected glucagon. Top line is intramuscular, bottom line is intranasal.
Figure 8B:
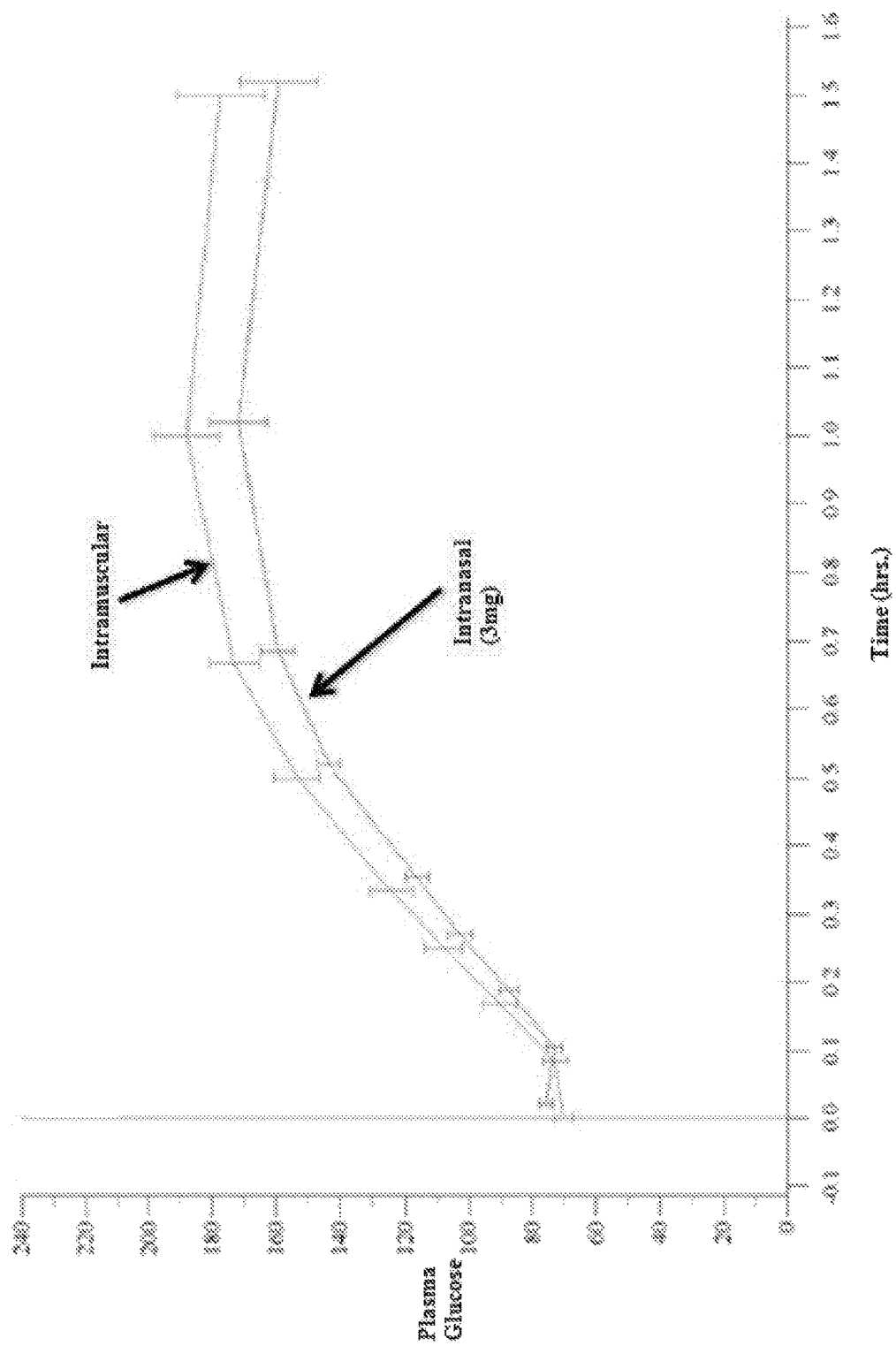
FIG. 8B: Average plasma glucose concentrations in children, ages 12-17, with type 1 diabetes treated with intranasal and injected glucagon. Top line is intramuscular, bottom line is intranasal.

Intranasal administration to children with type 1 diabetes with induced hypoglycemia of the Jorgensen 1991/Rosenfalck 1992 powder formulation is reported to increase plasma glucose concentration soon after dosing to peak levels 25-30 minutes post-dosing after which glucose levels decreased, compared with plasma glucose levels that continued to rise for at least 45 minutes after SC injection (Stenninger, 1993). Peak post-treatment glucagon values occurred at approximately 10 minutes after intranasal dosing (Rosenfalck 1992; Stenninger 1993). In contrast to the glucose profile observed with the Jorgensen 1991/Rosenfalck 1992 formulation, data generated in children (12-<17 years) with the powder formulation described in this invention show plasma glucose concentrations that continue to rise for at least 60 minutes after dosing (FIG. 8B). In addition, the peak plasma glucagon concentrations did not occur until approximately 20 minutes post-dosing (FIG. 8A).

Since episodes of severe hypoglycemia are unpredictable and could occur in insulin-using persons who are affected with nasal congestion, a study was conducted to evaluate the PK and PD of the invented powder formulation in this situation. As described in Experiment 11 and shown in FIGS. 9A and 9B, the pharmacokinetics and pharmacodynamics resulting from treatment with the nasal powder of this invention are not adversely affected by nasal congestion. This supports the utility of this invention to treat episodes of severe hypoglycemia in people who may be suffering from nasal congestion. As was observed in people without nasal congestion, the time to peak plasma glucagon levels was approximately 20 minutes post-dosing. Data have never been reported to indicate whether or not the Jorgensen 1991/Rosenfalck 1992 formulation can be used in treating a person with nasal congestion that could be seen in people suffering from a common cold or seasonal allergic rhinitis.

Applicants believe that these differences in results arise from a structural difference between the claimed powder formulation and the Jorgensen 1991/Rosenfalck 1992 powder. As discussed below, cosolubilization of the phospholipid and cyclodextrin components followed by drying and powder formation results in formation of some structure that has a characteristic XRPD peak that is absent from either material alone. This peak is retained when glucagon is added to the composition. Without being bound by any particular theory, it is believed that the glucagon or glucagon analog associates with the micellar phospholipid in solution and maintains some association after drying, albeit without disrupting the structure formed by the phospholipid and cyclodextrin, and that this association better presents the glucagon for nasal absorption. Thus the claimed powder formulation is not simply an admixture of the three components, but rather contains unique physical structure that is detectable through X-ray powder diffraction techniques.

This understanding of the structure of the formulation of the invention is consistent with known information about the interaction of glucagon with phospholipids surfactants. Glucagon forms complex structures at a molar ratio of about 55:1 phospholipid:glucagon (Epand & Sturtevant, 1982). It has also been shown that glucagon can bind to 50 phospholipid molecules, and that 20 of them are closely bound (Epand & Sturtevant, 1981). Boesch et al (1980) and Brown et al (1981) report that the conformation of glucagon bound to various micellar lipids, including DPC, is largely independent of the type of the lipid. The conformation is described as a well-defined, and predominantly extended. The stoichiometry of the DPC:glucagon complex was reported as 40:1. They also suggest the conformation of glucagon bound to micelles is very similar to that of glucagon bound to lipid bilayers.

The mole ratio of phospholipid (DPC, DDPC, LLPC, DSPC or DLPG): glucagon at a 10:10 weight ratio as in some of the preferred formulations of the invention between 6:1 and 10:1, suggesting that the phospholipids are most likely closely bound to glucagon in the intranasal powder formulations.

X ray powder diffraction studies on the powder formulation of the present invention clearly show the presence of a peaks likely to be associated with a micellar or mesophase structure in the formulation. These peaks are characterized low diffraction angles (6.6° 2θ for DPC and 7.3° 2θ for DDPC). (FIG. 6) These same peaks are seen in samples in which glucagon is not included, and are referred to in this application as "XRPD mesopeaks." This XRPD mesopeak is characteristic of the powder formulations of the invention.

Figure 6:
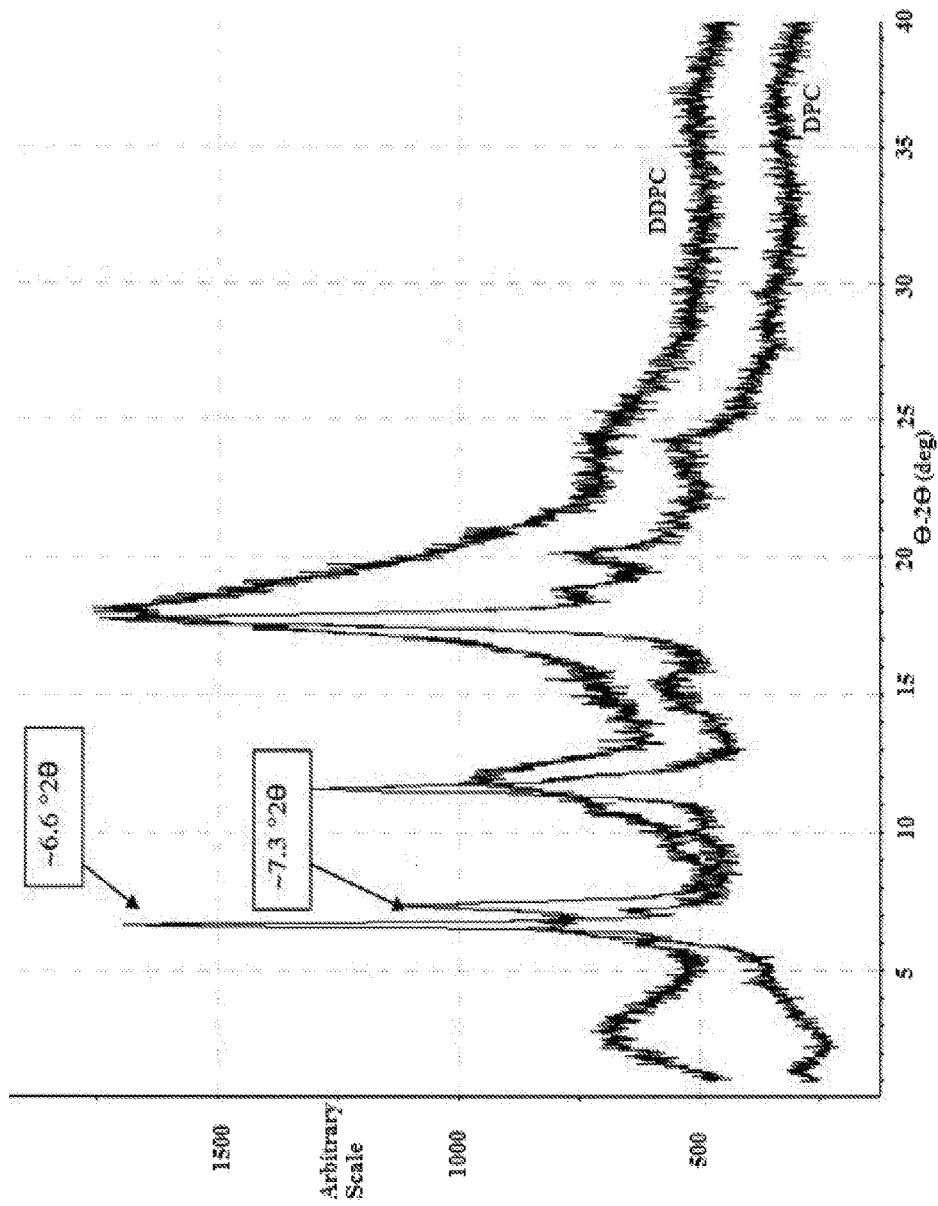
FIG. 6: X-ray powder diffractograms of powder formulations of glucagon: DPC: ß-CD and of glucagon-DDPC-ß-CD at a weight ratio of 10:10:80.

FIG. 6 presents overlayed X-ray powder diffraction results for glucagon-DPC-ß-cyclodextrin (File 474320) and glucagon-DDPC-ß-cyclodextrin (File 407476) compositions. The diffraction pattern retains high angle peaks consistent with the presence of crystalline cyclodextrin (e.g the peak 61 at around 18-20°-2θ), which is not unexpected since the cyclodextrin is present in substantial excess relative to phospholipid and glucagon. In addition, each pattern has a low diffraction angle peak at 6.6 and 7.3°-2θ, respectively. These peaks are also present in samples without glucagon that are made by solubilizing the phospholipid at micelle forming concentrations, adding the cyclodextrin and then drying the resulting solution. As used in this application, the statement that "at least a portion of the powder is present in a phase characterized by an XRPD mesopeak as determined by x-ray powder diffraction" indicates that the low angle peaks are detectable in the x-ray powder diffractogram, and clearly distinguishable from the noise of the measurement. In preferred embodiments, the size of the XRPD mesopeak (as determined by peak height) is about 30% of the height of the peak at about 18-20°-2θ (as in the pattern for File 407476 in FIG. 6) or greater, and may be about equal to the height of this peak (as in the pattern for File 474320 in FIG. 6).

The formation of a phase characterized by an XRPD mesopeak has been observed in samples with and without glucagon, and using different formulations and drying techniques. It has been observed that some variation in shape and position of the XRPD mesopeak can occur dependent on the conditions of drying. For example, lyophilization of larger amounts that leads to a thicker frozen layer and longer drying times was observed in one experiment to lead to formation of two broadened and overlapping XRPD mesopeaks.

A further benefit of the present invention is its usefulness as an emergency treatment, even under extreme environmental conditions, particularly cold conditions. The formulation of the invention remains directly useable even when the temperature is below freezing and tests have shown that powder stored at −20° C. can be used directly with acceptable delivery and uptake of glucagon. In contrast, emergency kits that contain a liquid carrier for reconstitution of glucagon prior to use must be maintained above the freezing point of the carrier. Likewise, glucagon solutions must also be maintained above the freezing point of the solution, which will be at a higher temperature if a solvent such as DMSO is used to provide solution stability.

Method of Making the Compositions of the Invention

A further aspect of the present invention is a method for preparing a powder formulation having glucagon-activity comprising glucagon or a glucagon analog, a cyclodextrin, and a phospholipid surfactant wherein at least a portion of the powder is present in a phase characterized by an XRPD mesopeak as determined by x-ray powder diffraction. The method comprises the steps of
  a. forming a first mixture of the glucagon and the surfactant in an aqueous carrier, wherein the surfactant is present as a concentration greater than or equal to the critical micelle concentration;
  b. adding the cyclodextrin to the first mixture to form a second mixture;
  c. drying the second mixture to form a solid formulation; and
  d. processing the solid formulation to produce a uniform powder, said uniform powder including at least a portion the powder in a phase characterized by an XRPD mesopeak.

Step a, forming a first mixture, can be accomplished by adding glucagon or a glucagon analog to a solvent, for example water, and then adding the surfactant. Alternatively, the surfactant may be solubilized first followed by addition of the glucagon or glucagon analog. The two components of the mixture may also be individually solubilized and then combined to form the first mixture.

Preferably, the solvent is acidified to a pH of 4 or less to enhance the solubility of the glucagon. The acidification can be accomplished with a mineral acid, such as HCl, phosphoric acid or sulfuric acid, or an organic acid such as acetic acid, citric acid glycolic acid or lactic acid, or using a combination of a mineral acid and an organic acid. In preferred formulations, the acid is acetic acid.

The amount of solvent used to form the first mixture is sufficient to solubilize the glucagon and phospholipid surfactant in the first mixture. Excess solvent can be used, although large excesses increase the amount of time and energy needed in the drying step and are therefore not preferred.

The cyclodextrin can be added to the first mixture as a solid, or in a solvent, such as water to form the second mixture. Mixing can be carried out by methods including static and dynamic mixing. Dynamic mixing can be done by use of a blade inserted into the liquid, which is attached to shaft and rotated by a motor. Static mixing can be carried out by flowing the liquid through a tortuous path inside a static mixer. The presence of an air-water interface during mixing under high speed mixing conditions may result in foaming. The high speed mixing may also, in turn, result in destabilization of the protein due to the shear stress. In order to minimize foaming, and preferably eliminate it, low speed mixing conditions are preferred. In the case of dynamic mixing, the speed is determined by the revolutions-per-minute (rpm) of the stirrer. Preferred rpm values are between 100 to 1000. In the case of static mixing, the low shear conditions are obtained by selecting a pump that allows for a non-laminar flow.

The second mixture is dried to remove the solvent (for example, water) and leave a solid product. Drying can be performed by freeze-drying, spray-drying, tray-drying or other techniques. The macroscopic physical characteristics of the product will vary depending on the drying technique, and may be in the form of a flaky solid from freeze drying or a dried solid cake. Regardless of the method used in drying, removal of excess water from the formulation has important effects on powder characteristics and stability.

Powders with excessive moisture content may be sticky and form clumps resulting in a powder that is difficult to manipulate for filling of an administration device. Importantly, the level of residual water content has a direct impact on the stability. In the case of glucagon, it is well understood that the stability and physical characteristics are adversely affected by water. Specifically, in the presence of excess water, glucagon forms amyloid fibrils that adversely affect the stability and toxicity profile of glucagon. (Pederson 2010). Because of this propensity to form amyloid fibrils, currently available glucagon products are supplied as a powder to be dissolved in water immediately before use. Water can also adversely affect the stability of glucagon due to hydrolysis, oxidation and deamidation. To this end, data generated with the formulations of the invention indicate that residual moisture content levels in excess of 5% in the bulk powder results in reduced stability compared to powder with residual water content below 5%. Suitable powders for nasal administration therefore typically have residual water content levels below 5%.

Suitable powders for nasal administration typically have particle size distributions such that most particles are greater than approximately 10 microns and smaller than approximately 1000 µm. Preferably, particle size distributions will be such that the D10 falls within the range of 3-75 µm, the D50 falls within the range of 15 to 450 µm, and the D90 falls within the range of 80-1000 µm, with a span of 1.5 to 15.

Suitable powders for nasal administration require physical characteristics that permit adequate flowability to allow for filling them into a nasal discharge device. Flowability is determined by various parameters including particle size, shape, density, surface texture, surface area, density, cohesion, adhesion, elasticity, porosity, hygroscopicity, and friability.

Powders with the appropriate particle size and flowability characteristics may be produced by processing the bulk power to remove particles that are too small or too large. Methods of processing the bulk powder to remove the particles that are too small or too large may include milling the bulk powder to break up larger particles and sieving to isolate the particles of the desired particle size range. Various methods of sieving may be performed including throw-action sieving, horizontal sieving, tapping sieving, supersonic sieving and air circular jet sieving. Sieves may be used as single sieves of a fixed nominal aperture or the bulk powder may be processed through a series of sieves of progressively smaller apertures to obtain the desired particle size distribution. Sieves may be woven wire mesh sieves with nominal apertures ranging from 25-1000 µm.

Spray pattern and plume geometry resulting from administration of the powder with a nasal powder administration device are important characteristics that govern the surface area upon which the nasal powder is deposited within the nasal cavity. Suitable spray pattern characteristics for the invention include a minimum diameter (Dmin) of 5-25 mm, a maximum diameter (Dmax) of 10 to 60 mm, and an ovality ratio of 0.5 to 6. Specific spray patterns observed for formulations of the invention are summarized in the following Table

| Spray Pattern | | | | | |
|---|---|---|---|---|---|
| Dmin (mm) | | Dmax (mm) | | Ovality ratio | |
| (min/max) | (mean) | (min/max) | (mean) | (min/max) | (mean) |
| 10.7-21.9 | 13.9 | 14.5-42.9 | 23.6 | 1.1-3.6 | 1.7 |

Suitable plume geometry characteristics for the invention include a spray angle falling within the range of 20 to 75° and a plume width falling within the range of 10 to 50 mm. The following table summarizes the plume geometry information for multiple lots of powder in accordance with the invention.

| Plume Geometry | | | |
|---|---|---|---|
| Spray Angle (°) | | Plume Width (mm) | |
| (min/max) | (mean) | (min/max) | (mean) |
| 28.31-65.2 | 44.8 | 15.2-38.4 | 25.0 |

Administration of and Applicators for the Composition of the Invention

While any methodology for introducing the powder into a user's nose may be used in the method of the invention, the powder composition of the invention is suitably provided in a purpose-designed nasal applicator that maintains the powder in a clean, dry and usable state until use, and then delivers the powder to the nasal mucosa of a user. Such applicators are known in the art, and generally have a powder formulation reservoir, and a powder formulation contained within the reservoir, and a mechanism for expelling the powder formulation from the reservoir through a nozzle receivable within a nostril.

The applicator is selected to be able to provide sufficient powder formulation in a single insufflation/administration to provide a therapeutic dose. Larger reservoirs and delivery capacity are required for powders with lower percentages of glucagon or glucagon analog in the formulation, while smaller reservoirs and delivery capacity can be used with higher percentage formulations.

Figure 10:
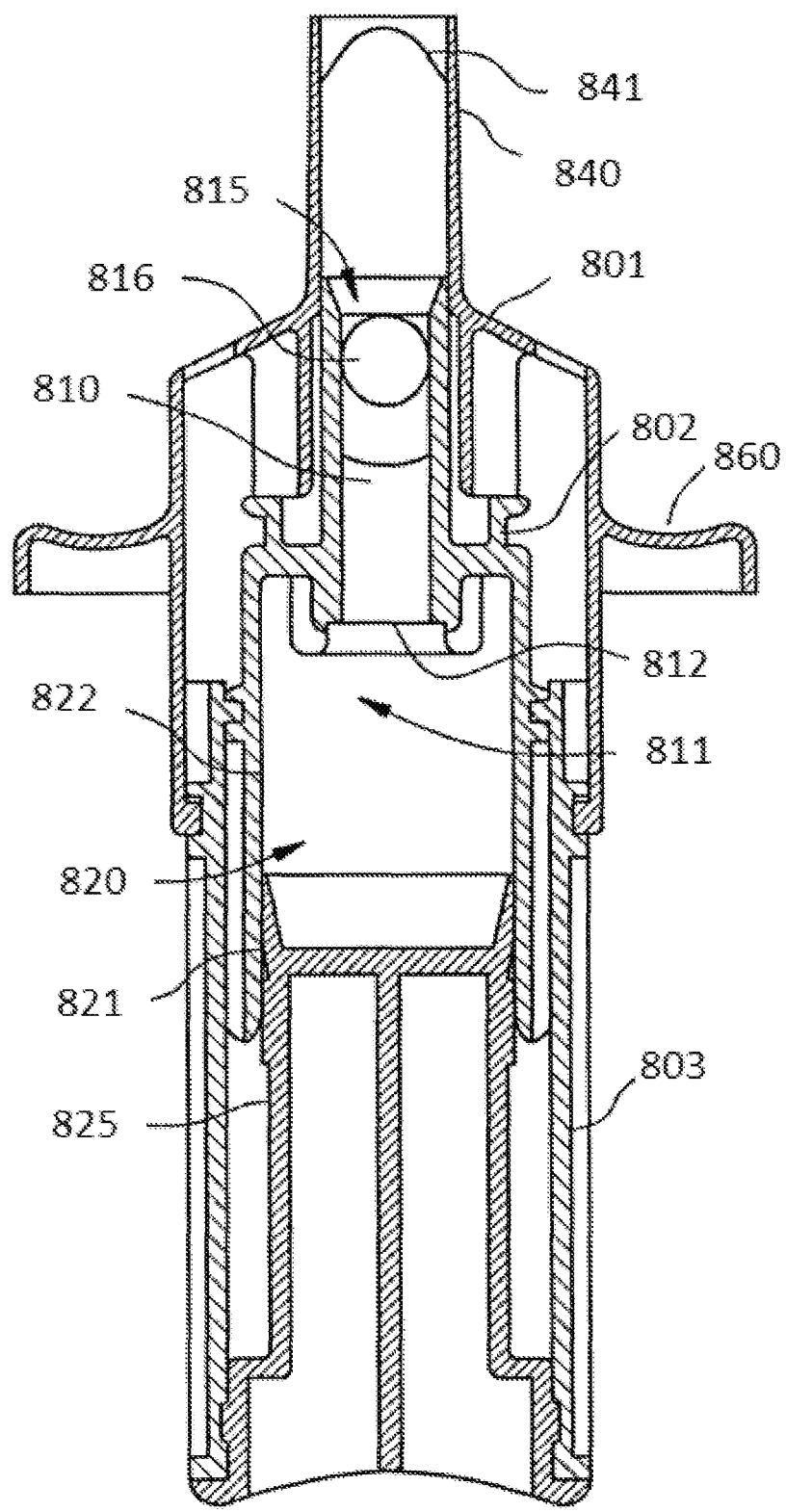
FIG. 10: Exemplary application device for nasal powder formulations (Aptar device).

Specific suitable delivery devices are disclosed in U.S. Pat. Nos. 6,398,074 and 6,938,798, which are incorporated herein by reference. FIG. 10 is taken from the '074 patent to illustrate a suitable device. In FIG. 10, reservoir 810 contains a single dose of a formulation in accordance with the present invention. The reservoir 810 has an air inlet 811 and a product outlet 815. A product retention device 812 and/or 813 is disposed in the air inlet 811 to keep the product in the reservoir 810 until dispensation of the product. The product outlet 815 is blocked, preferably in a sealed fashion, by a closing ball 816 which is removed from its blocking position by the flow of air when the product is being dispensed.

When a user actuates the device, he exerts a pressure on the plunger 825 in such a way that the piston 821 compresses the air contained in the chamber 822 of the air blast 820. Since grid 812 is permeable to air, the compression of the air in chamber 822 is transmitted to the reservoir 810 and consequently is applied to the closing ball 816 which is blocking the product outlet 815. The dimensions of the closing ball 816 and its fixing at the reservoir product outlet 815 are such that the ball 816 is removed from its blocking position, when a minimum predetermined pressure is created through the reservoir 810 in said air blast 820. Hence, when this minimum pressure is reached, the ball is suddenly moved towards the outlet channel 840 of the device and the flow of air created by the air blast 820 expels all of the dose contained in the reservoir 810. The pre-compression created by this closing ball 816 ensures that when it is removed from its blocking position, the energy accumulated in the hand of the user is such that the piston 821 integral with the plunger 825 is propelled within the chamber 822 thereby creating a powerful air flow, that is to say an air flow suitable to finely spray the dose of product and notably to get rid of any product agglomerates if it is a powder product.

Another example of an applicator device suitable for use in combination with the powder composition of the invention is that disclosed in US Patent Publication No. 20110045088, which is incorporated herein by reference. The device shown in U.S. Pat. No. 7,722,566 could also be used, particularly as shown in FIGS. 1 and 7 thereof, since administration into both nostrils is not required using the powder of the invention.

Still further examples of applicator devices for nasal administration of a powder composition are known from WO2014004400, and U.S. Pat. No. 5,702,362, which are incorporated herein by reference.

EXPERIMENTAL

Example 1

Glucagon, DPC and α-CD, ß-CD, or HP-ß-CD were dissolved in either a 0.01 N or a 0.1 N HCl solution. Formulations were also prepared with either 1 M acetic acid or 0.5 M acetic acid. The weight ratio of glucagon:DPC: cyclodextrin ranged from 5:10:75 to 10:20:70. In two separate experiments, either sodium citrate or citric acid was added as an additive. The lyophilized powder was packaged into a device for delivery to the nostril. The powder was delivered to Beagle dogs intranasally at a dose of 500 µg, 750 µg or 1000 µg. The powder was administered to either 3 or 6 dogs per group. Plasma glucose concentration was measured by using a glucometer. The plasma glucose concentrations prior to administration (0 min), and 5, 10, 20, 30, 40 and 60 minutes after nasal administration are shown in Table 1. In Table 1, Ratio refers to the ratio of glucagon: DPC:cyclodextrin, or to the ratio of glucagon:DPC:cyclodextrin:additive.

TABLE 1

Average plasma glucose concentrations (mmol/L) in the Beagle dog after intranasal administration of glucagon:DPC:CD compositions.

| Ratio | CD | Dose per nostril (μg) | Nostrils | Acid | Additive | 0 min | 5 min | 10 min | 20 min | 30 min | 40 min | 60 min |
|---|---|---|---|---|---|---|---|---|---|---|---|---|
| 5:25:70 | α-CD | 500 | 1 | 0.1N HCl | None | 3.7 | 3.4 | 6.1 | 6.3 | 3.6 | 2.4 | 3.4 |
| 5:25:70 | α-CD | 750 | 1 | 0.1N HCl | None | 3.7 | 3.7 | 4.4 | 4.7 | 6.9 | 5.0 | 3.8 |
| 5:25:70 | α-CD | 1000 | 1 | 0.1N HCl | None | 3.7 | 3.9 | 4.8 | 7.9 | 5.8 | 3.5 | 3.2 |
| 5:25:70 | α-CD | 500 | 2 | 0.1N HCl | None | 3.3 | 3.3 | 3.7 | 4.1 | 4.0 | 3.2 | 3.5 |
| 5:40:55 | α-CD | 500 | 1 | 0.1N HCl | None | 3.7 | 3.6 | 3.8 | 3.8 | 3.5 | 4.2 | 4.2 |
| 5:40:55 | α-CD | 1000 | 1 | 0.1N HCl | None | 3.6 | 3.6 | 4.3 | 6.7 | 5.1 | 3.8 | 3.2 |
| 5:25:70 | α-CD | 750 | 1 | 0.1N HCl | None | 3.7 | 3.5 | 4.2 | 4.3 | 4.3 | 4.1 | 4.0 |
| 10:30:60 | HP-β-CD | 750 | 1 | 0.1N HCl | None | 3.7 | 4.2 | 5.2 | 5.4 | 5.0 | 4.4 | 3.9 |
| 10:30:60 | HP-β-CD | 750 | 1 | 0.1N HCl | None | 3.4 | 4.2 | 5.2 | 5.1 | 4.9 | 4.0 | 3.7 |
| 10:70:10:10 | α-CD | 750 | 1 | 0.1N HCl | Citric acid | 3.6 | 5.2 | 6.0 | 6.2 | 5.9 | 4.5 | 3.3 |
| 10:70:10:10 | α-CD | 750 | 1 | 0.1N HCl | Sodium citrate | 3.7 | 5.4 | 6.6 | 6.3 | 5.5 | 4.4 | 3.9 |
| 10:10:80 | α-CD | 750 | 1 | 0.1N HCl | None | 3.8 | 5.6 | 7.3 | 9.0 | 8.0 | 6.0 | 3.1 |
| 10:10:80 | α-CD | 750 | 1 | 0.1N HCl | None | 4.0 | 4.1 | 5.1 | 5.6 | 6.1 | 6.1 | 5.7 |
| 5:10:85 | α-CD | 750 | 1 | 0.1N HCl | None | 3.9 | 3.8 | 4.4 | 4.2 | 4.1 | 4.0 | 4.0 |
| 10:10:80 | β-CD | 750 | 1 | 0.1N HCl | None | 3.8 | 4.7 | 7.0 | 7.7 | 8.1 | 6.7 | 5.2 |
| 10:10:80 | α-CD | 600 | 1 | 0.01N HCl | None | 4.0 | 4.3 | 5.7 | 5.6 | 5.5 | 4.6 | 4.0 |
| 10:10:80 | β-CD | 750 | 1 | 0.01N HCl | None | 4.5 | 5.1 | 6.6 | 7.2 | 6.8 | 5.5 | 4.8 |
| 10:10:80 | β-CD | 600 | 1 | 0.01N HCl | None | 4.0 | 4.3 | 5.4 | 4.9 | 4.9 | 3.6 | 3.7 |
| 10:10:80 | β-CD | 1000 | 1 | 0.01N HCl | None | 4.4 | 7.4 | 8.7 | 8.8 | 8.1 | 5.9 | 4.6 |
| 10:10:80 | β-CD | 750 | 1 | 0.01N HCl | None | 4.4 | 5.4 | 6.8 | 6.1 | 5.1 | 4.0 | 4.0 |
| 10:10:80 | β-CD | 500 | 1 | 0.01N HCl | None | 4.4 | 5.4 | 7.3 | 6.6 | 6.1 | 4.9 | 4.3 |
| 10:10:80 | β-CD | 500 | 1 | 1M acetic acid | None | 4.40 | 5.08 | 6.00 | 5.80 | 5.17 | 4.65 | 4.53 |
| 10:10:80 | β-CD | 1000 | 1 | 1M acetic acid | None | 3.80 | 5.08 | 8.22 | 9.74 | 10.0 | 7.96 | 6.44 |
| 10:10:80 | β-CD | 2000 | 1 | 1M acetic acid | None | 4.23 | 6.50 | 10.2 | 12.3 | 12.7 | 11.2 | 8.85 |

All compositions (prepared with different concentrations of the acid, different acids, different ratios of the three ingredients, in the presence of citric acid or sodium citrate, different doses, delivered to one nostril or to both nostrils) show an increase in plasma glucose concentration for up to between 10 and 30 minutes, followed by a decrease at 40 minutes, and followed by a further decrease at 60 minutes. As an example, results from a 10:10:80 composition with ß-CD and 0.01 N HCl administered at a 1000 μg dose to one nostril are shown in FIG. 1.

Example 2

Glucagon, DDPC, and α-CD, ß-CD, or hydroxylpropyl-ß-CD were dissolved in either a 0.01 N or a 0.1 N HCl solution. The weight ratio of glucagon:DDPC:cyclodextrin ranged from 5:10:75 to 10:20:70. In one study, sodium citrate was also added. The powder was packaged into a device for delivery to the nostril. The powder was delivered to Beagle dogs intranasally at a dose of 500 μg, 750 μg or 1000 μg. The powder was administered to either 3 or 6 dogs per group. Plasma glucose concentration was measured by using a glucometer. The results are shown in the following table. The plasma glucose concentrations prior to administration (0 min), and 5, 10, 20, 30, 40 and 60 minutes after nasal administration are shown in Table 2. In Table 2, Ratio refers to the ratio of glucagon:DDPC:cyclodextrin, or to the ratio of glucagon:DDPC:cyclodextrin:additive.

TABLE 2

Average plasma glucose concentrations (mmol/L) in the Beagle dog after intranasal administration of glucagon:DDPC:CD compositions.

| Ratio | CD | Dose per nostril (μg) | Nostrils | Acid | Additive | | 0 min | 5 min | 10 min | 20 min | 30 min | 40 min | 60 min |
|---|---|---|---|---|---|---|---|---|---|---|---|---|---|
| 5:10:85 | α-CD | 500 | 1 | 0.1N HCl | None | 5:10:85, α-CD, 500 μg, 1 nostril | 3.8 | 3.7 | 4.6 | 6.0 | 6.3 | 4.3 | 3.4 |
| 5:10:85 | α-CD | 750 | 1 | 0.1N HCl | None | 5:10:85, α-CD, 750 μg, 1 nostril | 3.6 | 3.8 | 7.8 | 7.6 | 8.3 | 4.7 | 3.3 |
| 5:10:85 | α-CD | 1000 | 1 | 0.1N HCl | None | 5:10:85, α-CD, 1000 μg, 1 nostril | 3.8 | 4.0 | 4.7 | 7.4 | 7.1 | 4.3 | 3.8 |
| 5:10:85 | α-CD | 500 | 2 | 0.1N HCl | None | 5:10:85, α-CD, 500 μg per nostril, 2 nostrils | 3.4 | 3.1 | 3.4 | 5.3 | 5.0 | 3.2 | 3.2 |

TABLE 2-continued

Average plasma glucose concentrations (mmol/L) in the Beagle dog after intranasal administration of glucagon:DDPC:CD compositions.

| Ratio | CD | Dose per nostril (µg) | Nostrils | Acid | Additive | | 0 min | 5 min | 10 min | 20 min | 30 min | 40 min | 60 min |
|---|---|---|---|---|---|---|---|---|---|---|---|---|---|
| 5:51:44 | α-CD | 500 | 1 | 0.1N HCl | None | 5:51:44, α-CD, 500 µg, 1 nostril | 3.3 | 3.2 | 4.0 | 4.6 | 4.3 | 3.6 | 3.9 |
| 5:51:44 | α-CD | 500 | 2 | 0.1N HCl | None | 5:51:44, α-CD, 500 µg per nostril, 2 nostrils | 3.4 | 2.8 | 4.0 | 4.8 | 3.8 | 3.6 | 3.7 |
| 5:10:85 | α-CD | 750 | 1 | 0.1N HCl | None | 5:10:85, α-CD, 750 µg, 1 nostril | 3.7 | 5.1 | 6.4 | 7.5 | 7.9 | 7.3 | 6.3 |
| 10:41:49 | HP-β-CD | 750 | 1 | 0.1N HCl | None | 10:41:49, HP-β-CD, 750 µg, 1 nostril | 3.7 | 3.5 | 4.1 | 4.0 | 4.0 | 3.8 | 3.9 |
| 10:41:49 | HP-β-CD | 750 | 1 | 0.1N HCl | None | 10:41:49, HP-β-CD, 750 µg, 1 nostril | 3.7 | 4.6 | 5.6 | 5.5 | 4.9 | 4.1 | 3.7 |
| 10:25:55:10 | α-CD | 750 | 1 | 0.1N HCl | Sodium Citrate | 10:25:55:10, α-CD, sodium citrate, 750 µg, 1 nostril | 3.6 | 4.8 | 6.3 | 6.3 | 5.5 | 4.6 | 4.0 |
| 10:20:70 | α-CD | 750 | 1 | 0.1N HCl | None | 10:20:70, α-CD, 750 µg, 1 nostril | 3.5 | 3.9 | 4.4 | 4.3 | 4.4 | 4.0 | 3.9 |
| 10:10:80 | α-CD | 750 | 1 | 0.1N HCl | None | 10:10:80, α-CD, 750 µg, 1 nostril | 3.5 | 5.3 | 6.7 | 7.8 | 6.7 | 5.3 | 3.7 |
| 10:10:80 | α-CD | 750 | 1 | 0.1N HCl | None | 10:10:80, α-CD, 750 µg, 1 nostril | 3.8 | 4.9 | 5.5 | 6.9 | 5.6 | 4.4 | 4.0 |
| 5:10:85 | α-CD | 750 | 1 | 0.1N HCl | None | 5:10:85, α-CD, 750 µg, 1 nostril | 4.0 | 4.3 | 5.2 | 5.6 | 5.6 | 5.6 | 5.2 |
| 10:10:80 | β-CD | 750 | 1 | 0.1N HCl | None | 10:10:80, β-CD, 750 µg, 1 nostril | 3.6 | 4.7 | 6.8 | 6.5 | 6.1 | 4.6 | 4.0 |
| 10:10:80 | β-CD | 700 | 1 | 0.1N HCl | None | 10:10:80, β-CD, 700 µg, 1 nostril | 4.0 | 5.5 | 7.1 | 6.9 | 7.0 | 5.2 | 4.3 |
| 10:10:80 | α-CD | 750 | 1 | 0.01N HCl | None | 10:10:80, α-CD, 750 µg, 1 nostril, 0.01N HCl | 4.3 | 4.7 | 6.0 | 6.4 | 6.5 | 5.1 | 4.5 |
| 10:10:80 | β-CD | 1000 | 1 | 0.01N HCl | None | 10:10:80, β-CD, 1000 µg, 1 nostril, 0.01N HCl | 4.2 | 6.4 | 8.7 | 8.5 | 7.5 | 4.6 | 3.6 |
| 10:10:80 | β-CD | 750 | 1 | 0.01N HCl | None | 10:10:80, β-CD, 750 µg, 1 nostril, 0.01N HCl | 4.5 | 6.1 | 6.4 | 6.4 | 5.8 | 4.4 | 3.9 |
| 10:10:80 | β-CD | 500 | 1 | 0.01N HCl | None | 10:10:80, β-CD, 500 µg, 1 nostril, 0.01N HCl | 4.4 | 5.8 | 6.8 | 5.4 | 4.6 | 4.0 | 4.1 |

Figure 2:
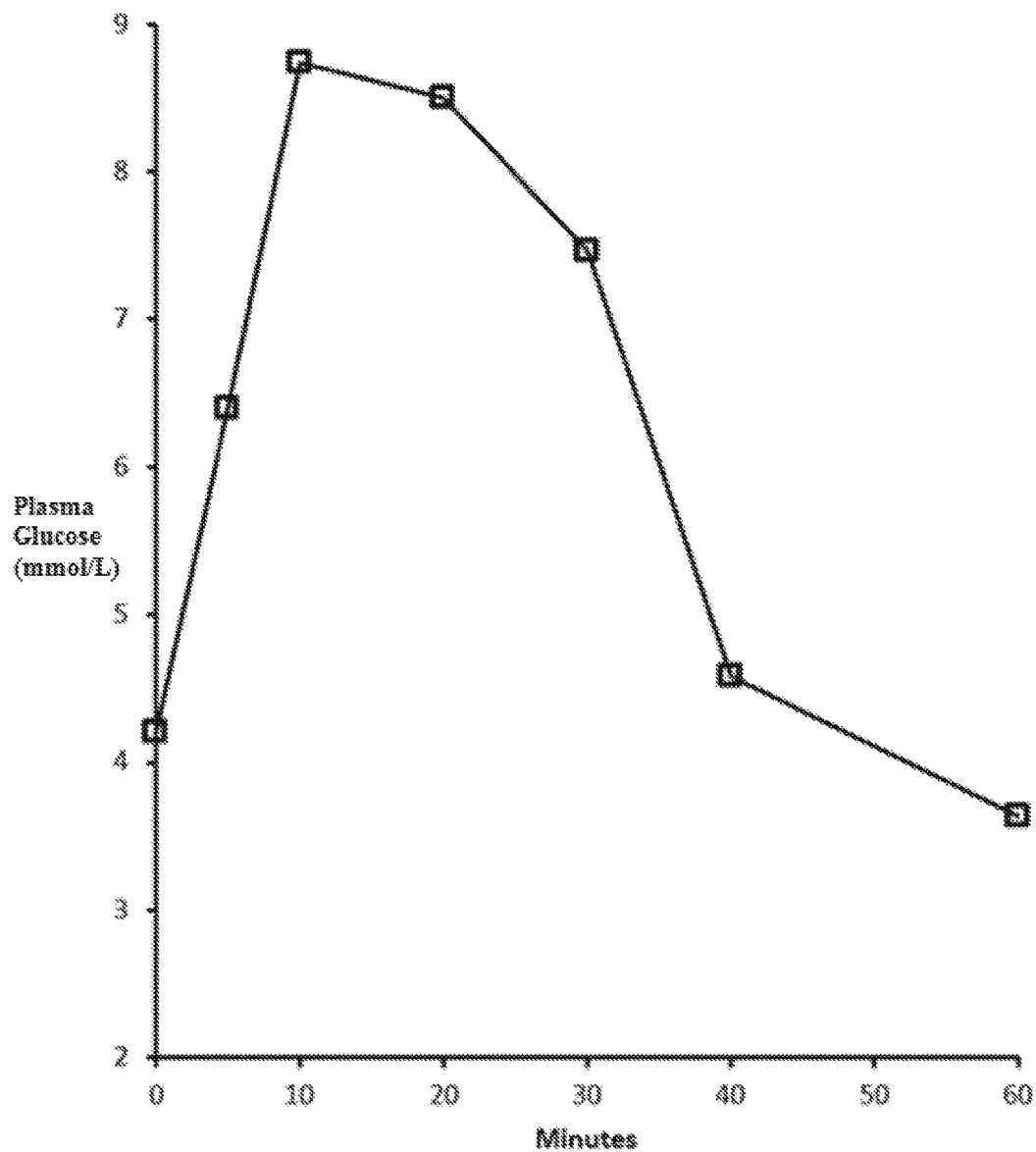
FIG. 2: Plasma glucose concentration in mmol/L over time upon intranasal administration to dogs at a 1 mg dose of glucagon via a powder formulation with a glucagon: DDPC: ß-CD weight ratio of 10:10:80.

All compositions (prepared with different concentrations of the acid, different cyclodextrins, different ratios, different doses, delivered to either one nostril or to both nostrils) show an increase in plasma glucose concentration for up to between 10 and 30 minutes, followed by a decrease at 40 minutes, and further followed by a decrease at 60 minutes. As an example, results from a 10:10:80 composition with ß-CD administered at a 1000 µg dose delivered to one nostril are shown in FIG. 2.

Example 3

Glucagon, LLPC and ß-CD were dissolved in either a 0.01 N or a 0.1 N HCl solution. The weight ratio of glucagon:LLPC:ß-CD was 10:10:80. The powder was packaged into a device for delivery to one nostril. The powder was delivered to Beagle dogs intranasally either at a dose of 750 µg or 1000 µg. The powder was administered to 6 dogs per group. Plasma glucose concentration was measured by using a glucose strip. The plasma glucose concentrations prior to administration (0 min), and 5, 10, 20, 30, 40 and 60 minutes after nasal administration are shown in Table 3.

TABLE 3

Average plasma glucose concentrations (mmol/L) in the Beagle dog after intranasal administration of glucagon:LLPC:CD compositions.

| Dose in µg | Acid | Plasma Glucose Concentration (mmol/L) | | | | | | |
|---|---|---|---|---|---|---|---|---|
| | | 0 min | 5 min | 10 min | 20 min | 30 min | 40 min | 60 min |
| 750 | 0.1N HCl | 3.8 | 4.8 | 6.6 | 6.9 | 6.1 | 4.4 | 4.0 |
| 750 | 0.1N HCl | 4.2 | 4.5 | 5.8 | 5.7 | 5.7 | 5.2 | 4.6 |
| 1000 | 0.01N HCl | 4.5 | 6.6 | 7.6 | 7.3 | 7.4 | 5.4 | 4.2 |

Figure 3:
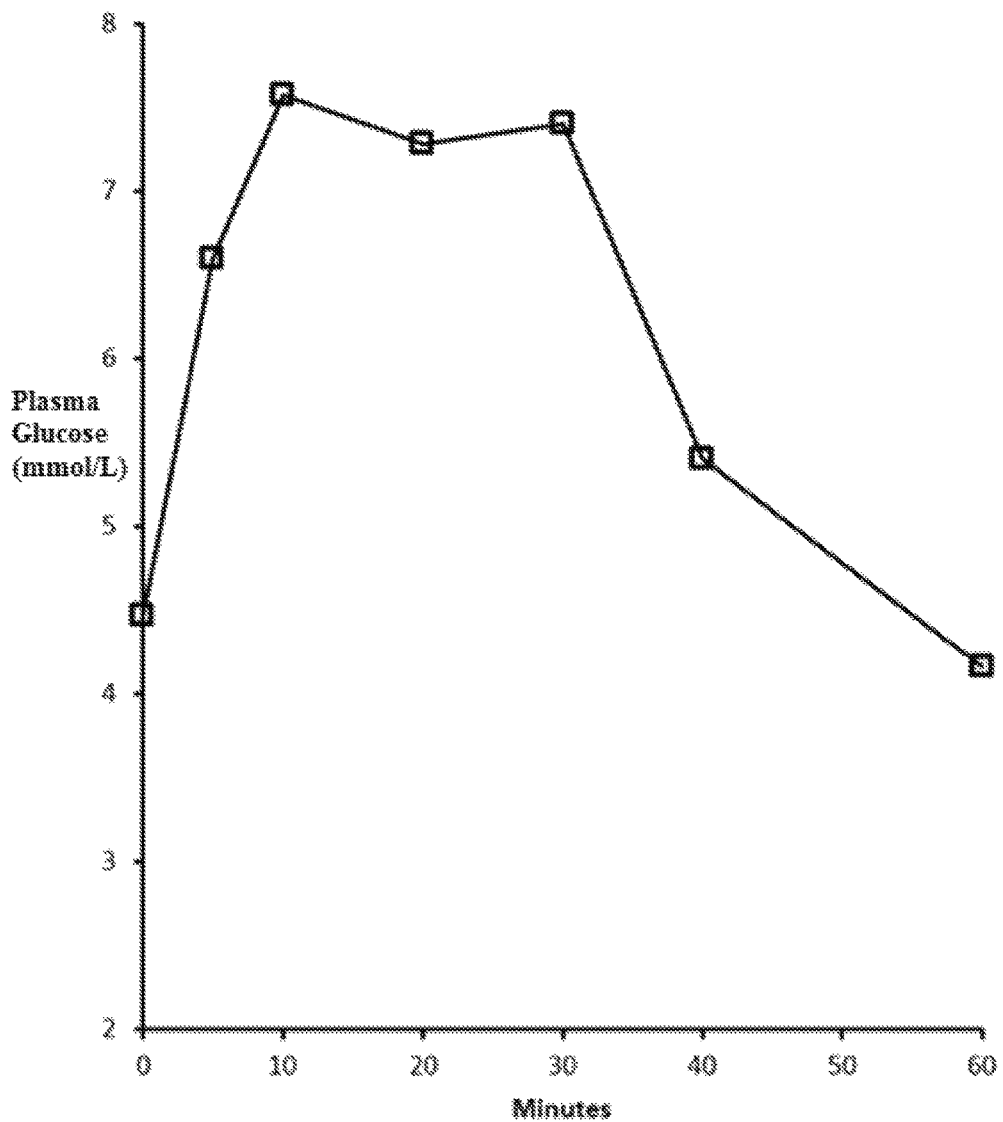
FIG. 3: Plasma glucose concentration in mmol/L over time upon intranasal administration to dogs at a 1 mg dose of glucagon via a powder formulation with a glucagon: LLPC: ß-CD weight ratio of 10:10:80.

All compositions (different doses, delivered to one nostril show an increase in plasma glucose concentration for up to between 10 and 20 minutes, followed by a decrease at either 30 or 40 minutes, and further followed by a decrease at 40 or 60 minutes. As an example, results from the 10:10:80 composition with ß-CD administered at a 1000 dose to one nostril is shown in FIG. 3.

Example 4

Glucagon, DSPC and ß-CD were dissolved in either a 0.01 N or a 0.1 N HCl solution. The weight ratio of glucagon:D8PC: ß-CD was 10:10:80. The powder was packaged into a device for delivery to the nostril. The powder was delivered to Beagle dogs intranasally. The powder was administered to 6 dogs per group. Plasma glucose concentration was measured by using a glucose strip. The plasma glucose concentrations prior to administration (0 min), and 5, 10, 20, 30, 40 and 60 minutes after nasal administration are shown in Table 4.

TABLE 4

Average plasma glucose concentrations (mmol/L) in the Beagle dog after intranasal administration of glucagon:D8PC:CD compositions.

| Acid | Plasma Glucose Concentration (mmol/L) | | | | | | |
|---|---|---|---|---|---|---|---|
| | 0 min | 5 min | 10 min | 20 min | 30 min | 40 min | 60 min |
| 0.1N HCl | 4.0 | 5.4 | 7.4 | 7.7 | 7.4 | 6.0 | 4.8 |
| 0.01N HCl | 3.5 | 4.0 | 4.8 | 4.5 | 4.3 | 4.0 | 3.9 |
| 0.01N HCl | 4.1 | 4.7 | 6.3 | 5.7 | 5.0 | 3.9 | 3.9 |
| 0.01N HCl | 3.7 | 4.3 | 5.4 | 5.4 | 5.3 | 4.7 | 4.4 |

Figure 4:
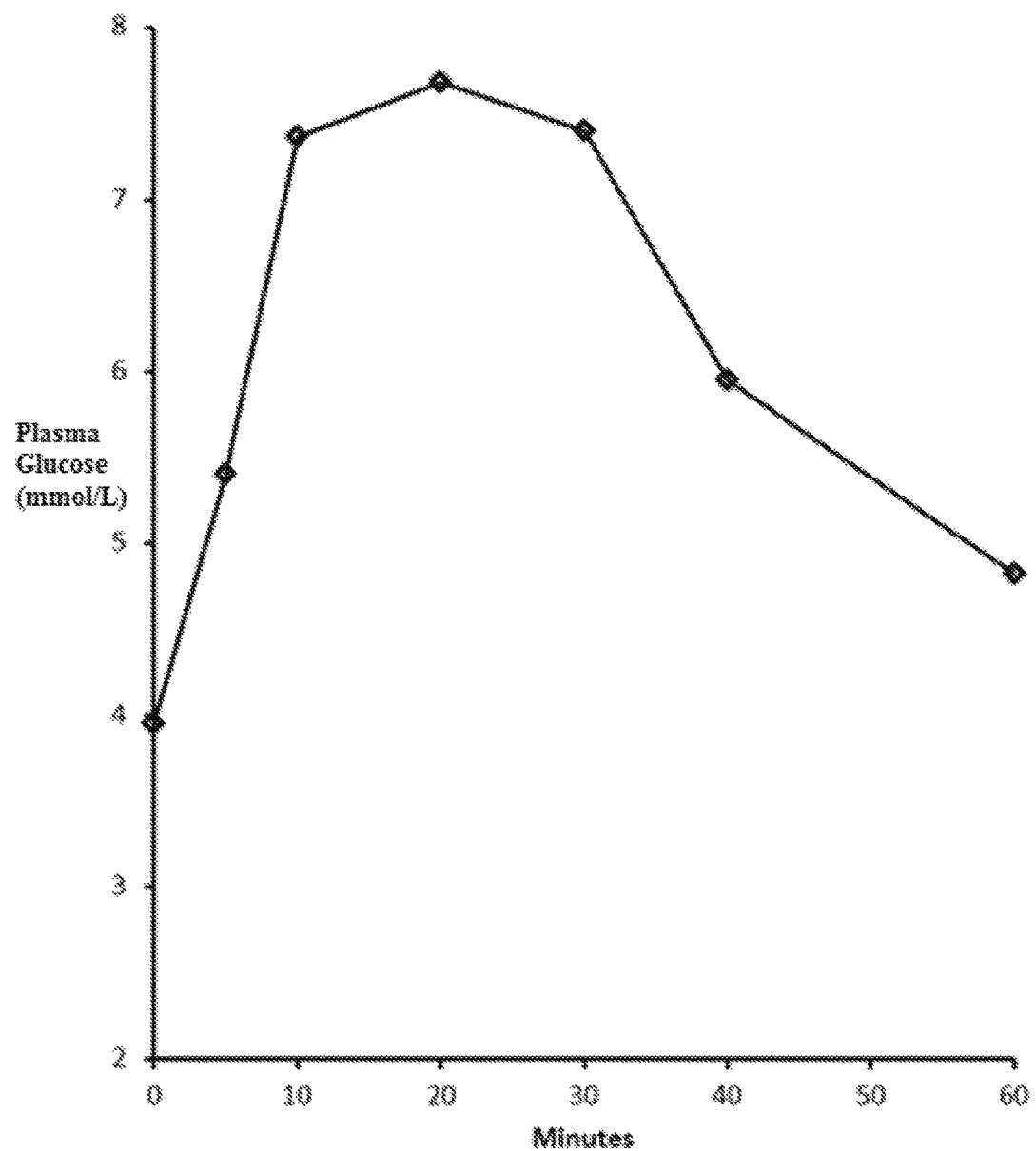
FIG. 4: Plasma glucose concentration in mmol/L over time upon intranasal administration to dogs at a 750 µg dose of glucagon via a powder formulation with a glucagon: D8PC: ß-CD weight ratio of 10:10:80.

All compositions (prepared with different concentrations of the acid delivered to one nostril) show an increase in plasma glucose concentration for up to between 10 and 20 minutes, followed by a decrease at 30 or 40 minutes, and further followed by a decrease at 40 or 60 minutes. As an example, results from the 10:10:80 composition with ß-CD administered at a 750 µg dose to one nostril are shown in FIG. 4.

Example 5

Glucagon, DLPG and α-CD were dissolved in a 0.1 N HCl solution. The weight ratio of glucagon:DLPG: α-CD was either 5:25:70 or 5:54:41. Separately, glucagon, DLPG and ß-CD were dissolved in 0.1 N HCl solution at a weight ratio of 10:10:80. The resultant solutions were lyophilized to produce a powder. The powder was packaged into a device for delivery to the nostril. The powder was delivered to either one nostril or both nostrils of Beagle dogs. The powder was administered to either 3 or 6 dogs. Plasma glucose concentration was measured by using a glucose strip. The results are shown in the following table. The weight ratio of glucagon:DLPG: α-CD (or, ß-CD), dose of glucagon per nostril, whether the powder was delivered to one or both nostrils are shown in the table. The plasma glucose concentrations prior to administration (0 min), and 5, 10, 20, 30, 40 and 60 minutes after nasal administration are shown in Table 5.

TABLE 5

Average plasma glucose concentrations (mmol/L) in the Beagle dog after intranasal administration of glucagon:DLPG:CD compositions.

| Ratio | CD | Dose per Nostril in µg | Nostrils | Plasma Glucose Concentration (mmol/L) | | | | | | |
|---|---|---|---|---|---|---|---|---|---|---|
| | | | | 0 min | 5 min | 10 min | 20 min | 30 min | 40 min | 60 min |
| 5:25:70 | α-CD | 500 | 1 | 3.9 | 3.9 | 4.1 | 4.0 | 4.6 | 4.4 | 4.1 |
| 5:25:70 | α-CD | 750 | 1 | 3.8 | 3.5 | 5.3 | 6.6 | 7.2 | 4.6 | 3.6 |
| 5:25:70 | α-CD | 1000 | 1 | 3.4 | 4.0 | 4.4 | 5.7 | 4.4 | 3.7 | 4.3 |
| 5:25:70 | α-CD | 500 | 2 | 3.8 | 3.1 | 3.1 | 3.2 | 4.3 | 4.1 | 4.0 |
| 5:54:41 | α-CD | 500 | 1 | 3.4 | 3.0 | 3.2 | 4.2 | 3.2 | 4.3 | 4.0 |
| 10:10:80 | β-CD | 750 | 1 | 4.2 | 4.7 | 6.1 | 6.0 | 5.5 | 4.6 | 4.0 |

Figure 5:
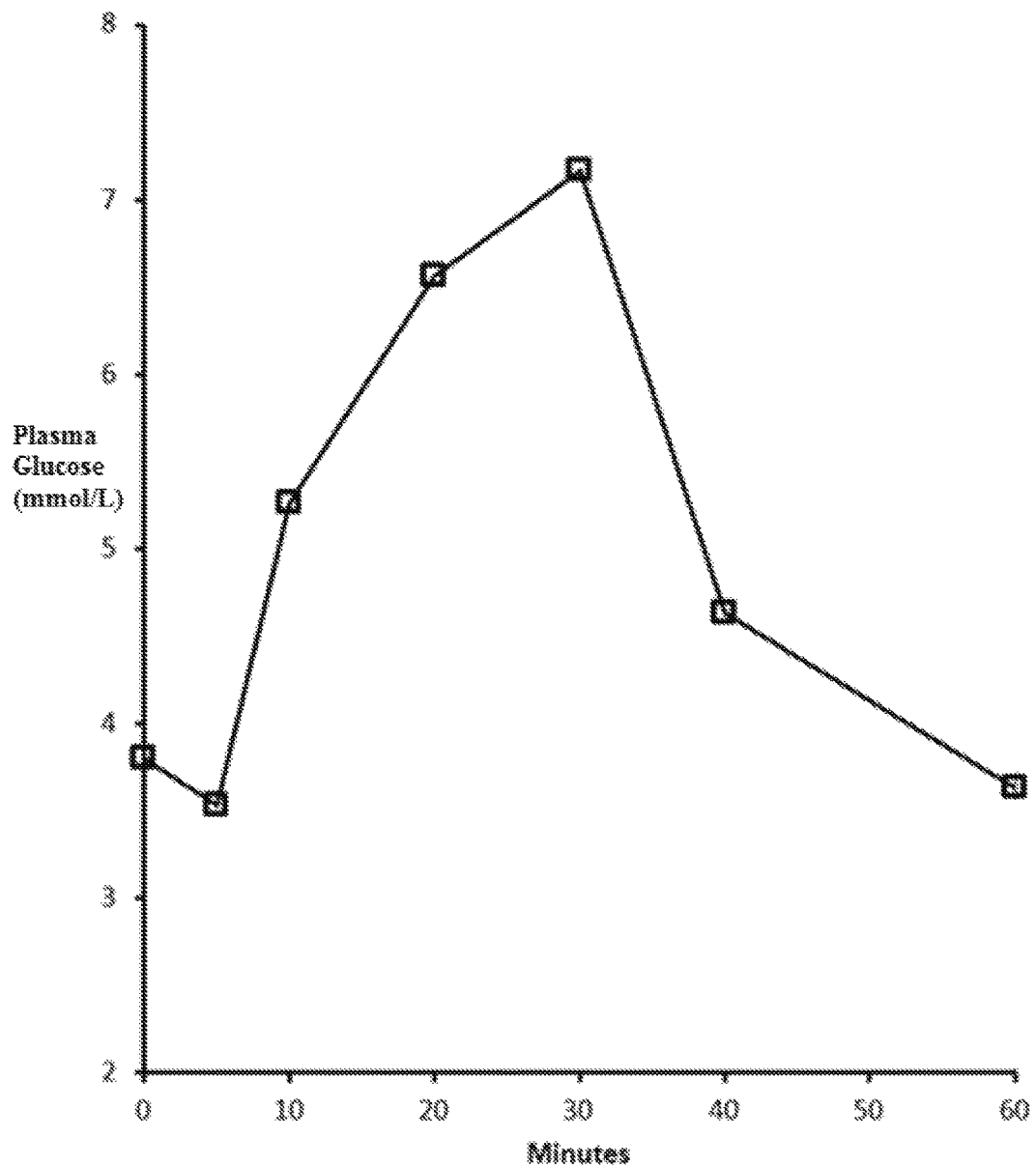
FIG. 5: Plasma glucose concentration in mmol/L over time upon intranasal administration to a single nostril of dogs at a 750 µg dose of glucagon via a powder formulation with a glucagon:DLPG: α-CD weight ratio of 5:25:70.

All compositions (prepared with different cyclodextrins, different ratios, different doses, delivered to either one nostril or to both nostrils) show an increase in plasma glucose concentration for up to between 10 and 30 minutes, followed by a decrease at 40 minutes, and further followed by a decrease at 60 minutes. As an example results from the 5:25:70 composition with α-CD administered at a 750 µg dose to one nostril, which resulted in the highest plasma glucose concentration, are shown in FIG. 5.

Example 6

X-ray powder diffraction was used to determine the structure of the glucagon-DPC-ß-cyclodextrin and glucagon-DDPC-ß-cyclodextrin compositions. They exhibit a peak at low angles (6.6° 2θ for DPC and 7.3° 2θ for DDPC) indicating a mesophase (FIG. 6). These peaks are absent for glucagon because it is an amorphous powder. They are also absent in ß-cyclodextrin which exhibits a characteristic crystalline form. Further they are absent in the surfactant, DPC. These peaks are present in mixtures of DDPC (or DPC) and ß-cyclodextrin, in the absence of glucagon. The compositions of the current invention are characterized by a mesophase detectable through these low diffraction angle peaks.

Example 7

The volume-weighted distribution profile is used to calculate $D_{10}$, $D_{50}$, and $D_{90}$ are presented in Table 6.

TABLE 6

Diameter of 10% of the particles ($D_{10}$), 50% of the particles ($D_{50}$), and 90% of the particles ($D_{90}$).

| Surfactant | Acid | $D_{10}$ (μm) | $D_{50}$ (μm) | $D_{90}$ (μm) |
|---|---|---|---|---|
| DDPC | 0.1N HCl | 6.063 | 11.77 | 21.86 |
| DPC | 0.1N HCl | 6.63 | 66.51 | 426 |
| DPC with sonication | 0.1N HCl | 3.6 | 10.68 | 21.77 |
| D8PC | 0.1N HCl | 7.926 | 17.97 | 35.34 |
| LLPC | 0.1N HCl | 8.031 | 15.31 | 28.89 |
| DPC | 1M acetic acid | 6.867 | 92.480 | 537.471 |

The particle size analysis shows that a minority of the particles in the six different powder formulations have an effective diameter ranging from 3.6 to 8.031 μm. The $D_{10}$ results show that greater than 90% of the particles in the powder delivered to the nostril cannot be inhaled.

Example 8

A powder formulation was prepared using the methods described in Method of Preparation. The composition was 10:10:80 glucagon:DPC:ß-cyclodextrin prepared using 1 M acetic acid. Ten milligrams of the powder contained 1 mg of glucagon. Ten milligrams of the powder formulation were packaged into each of ten devices. The powder delivered upon actuation of the device was collected. The weights of the delivered powder from the ten devices are shown in Table 7, as Delivered Dose (mg). The Uniformity of Delivered Dose (%) from the ten devices, also shown in Table 7, was calculated by multiplying by 100 the ratio of the amount of glucagon in each of the ten delivered powders to the amount of glucagon in 10 milligrams of the powder before it was filled into each of the ten devices.

TABLE 7

Delivered dose and uniformity of the delivered dose.

| Device Number | Uniformity of Delivered Dose (%) | Delivered Dose, mg |
|---|---|---|
| 1 | 97.5 | 9.3 |
| 2 | 97.0 | 9.2 |
| 3 | 98.9 | 9.7 |
| 4 | 102.7 | 9.8 |
| 5 | 100.3 | 9.7 |
| 6 | 92.3 | 9.0 |
| 7 | 100.2 | 9.6 |
| 8 | 96.9 | 9.2 |
| 9 | 94.8 | 9.2 |
| 10 | 96.8 | 9.2 |

Example 9

A multiple center, randomized, two-way, crossover Phase III study in which patients with type 1 diabetes (T1D, n=75) were enrolled to evaluate the effectiveness and safety of a single dose of intranasally administered glucagon (the powder that is the subject of this invention) compared to glucagon administered by IM injection following insulin-induced hypoglycemia was conducted. The primary endpoint in this study was the proportion of patients who achieved an increase in blood glucose levels to ≥70 mg/dL within 30 minutes of treatment with glucagon or a 20 mg/mL increment in blood glucose within 30 minutes of treatment with glucagon. The protocol used insulin to reduce blood glucose levels to the hypoglycemic range (target nadir of <50 mg/dL).

Statistical analysis of the glycemic response to treatment with the nasal powder showed that the nasal powder was non-inferior to injected glucagon in treating insulin-induced hypoglycemia. The glucose response curve, presented in FIG. 7, shows that glucose levels increased substantially in both the nasal and injected treated groups and that blood glucose levels increased to within the normal range in most subjects in both groups by about 15 minutes post-dosing.

Example 10—AMG103

AMG 103 was a study in children with type 1 diabetes, aged 4-<17 years. Induction of severe hypoglycemia in this population is not permitted by pediatric IRBs but insulin was used if necessary to normalize blood glucose to a target of <80 mg/dL (4.4 mmol/L) prior to dosing with glucagon.

Children visited the study facility twice. At the first visit, 12 children aged 12 to <17 years were randomized to glucagon by IM injection (dose rate according to the manufacturer's labeling) or to a glucagon powder formulation that is the subject of this invention (10:10:80 by weight). At the second visit, subjects received the alternative treatment. For children in the 4 to <8 years and 8 to <12 year age groups, there were 18 children per group. Within each of these age groups, children were randomized 2:1 to receive either two doses of intranasal glucagon or a single injection of glucagon IM. For the children receiving the IN glucagon, they were randomized to receive 2 or 3 mg on the first visit and the alternative dose level on the second visit. Study participants and the study site were blinded to the dose level.

Results from the children aged 12-<17 are provided as an example of what was seen in children dosed with nasal glucagon powder. FIG. 8A provides the glucagon PK curve while FIG. 8B provides the glucose profile. The data generated in this study indicate that nasal powder glucagon resulted in a glucose response that was no different than that observed after an injection of glucagon.

Example 11—Effect of Nasal Congestion

The powder of this invention consisting of glucagon:DPC and beta cyclodextrins in ratios of 10:10:80 by weight, was tested in subjects with common cold with and without concomitant administration of nasal decongestant in a study to investigate the safety and PK/PD of a 3 mg dose of IN glucagon in male and female subjects. This was a single center, single dose, open-label, repeated measures, parallel design study. All thirty-six (36) subjects received a single 3 mg dose of glucagon by intranasal route, in the morning after a 10-hour overnight fast. Cohort 1 (18 subjects) was scheduled for two periods. During Period 1, the subjects had nasal congestion and/or nasal discharge associated with a common cold and during Period 2, the subjects had recovered from the common cold and had been symptom free for at least 2 days. In Cohort 2 (Subjects #019 to 036), the subjects were scheduled for only Period 1. After presenting with nasal congestion and/or nasal discharge associated with a common cold, these subjects were pretreated with a nasal decongestant prior to receiving a single IN dose of glucagon.

Measurements of peak nasal inspiratory air flow provided an objective measurement of the nasal congestion and confirmed the nasal congestion associated with common cold as well as the intended therapeutic effect of oxymetazoline.

The study drug was well tolerated and there were no serious adverse events or deaths during this study.

Figure 9A:
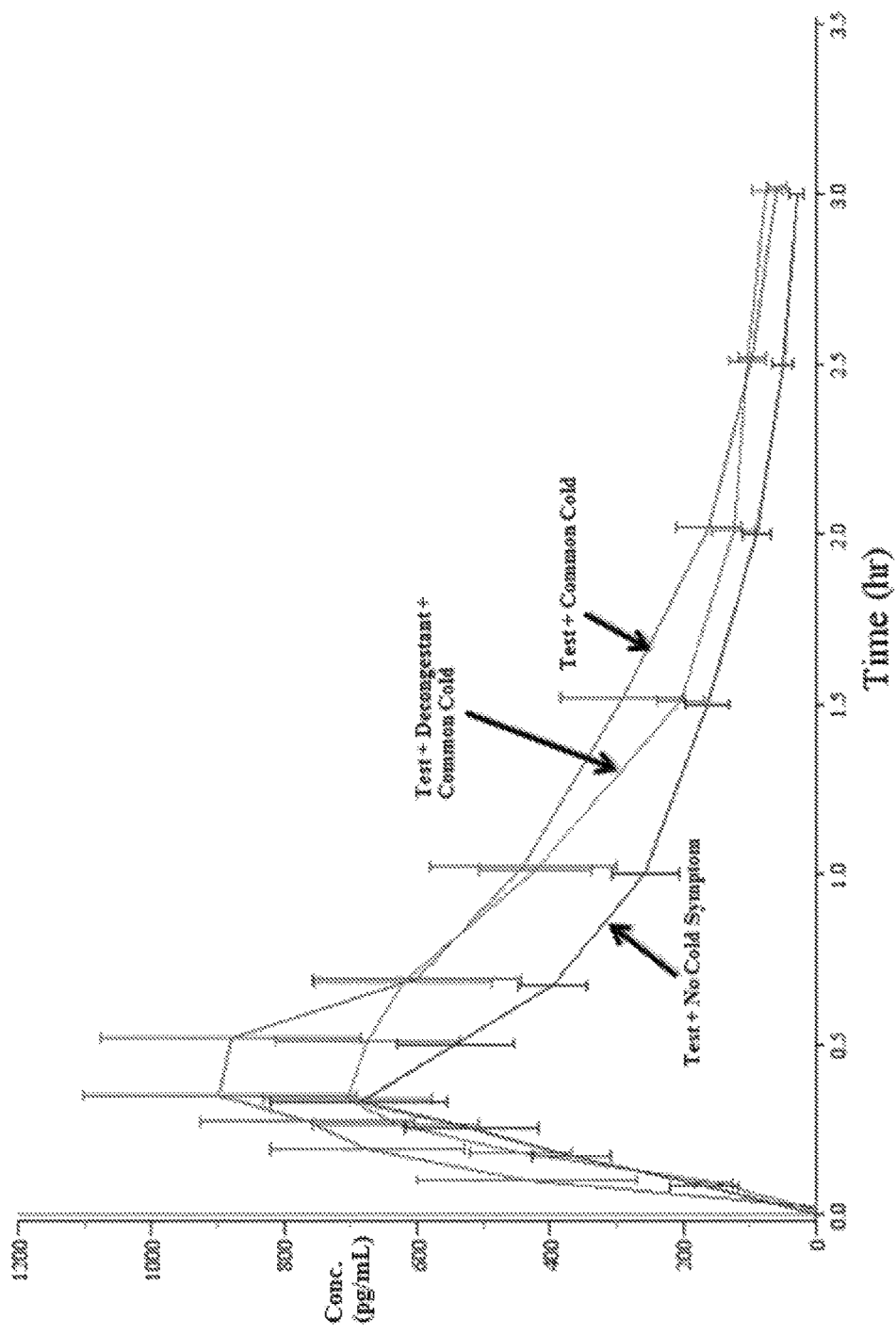
FIG. 9A: Average plasma glucagon concentrations in adults with (top line) and without nasal congestion (bottom line), and with congestion and pre-treatment with a nasal decongestant (middle line).
Figure 9B:
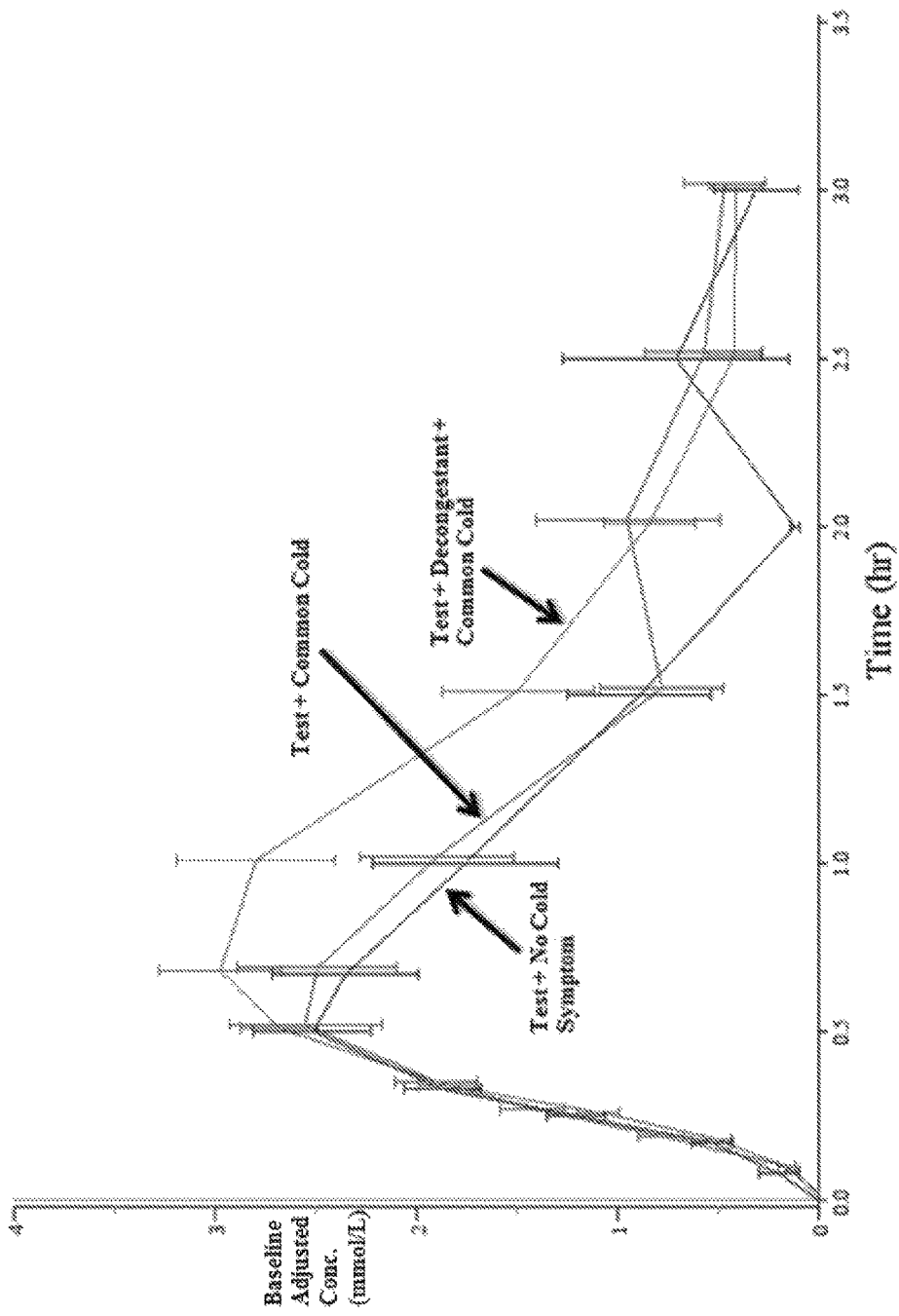
FIG. 9B: Average plasma glucose concentrations in adults with (top line) and without (bottom line) nasal congestion, with congestion and pre-treatment with a nasal decongestant (middle line).

The glucagon and glucose responses after administration of the powder are presented in FIGS. 9A and 9B. Plasma glucagon concentrations (FIG. 9A) increased substantially above baseline with mean peak concentrations ($C_{max}$) of 1198.4, 868.0 and 801.5 pg/mL for "AMG504-1+Common cold", "Common cold+Decongestant", and "No Cold Symptoms", respectively. Median time to peak concentrations ($t_{max}$) was 20 minutes post dose for all treatment groups. The estimated $AUC_{0-t}$ for 'AMG504-1+Common Cold' was higher than the other two treatment groups (1198.4 vs. 1038.0 and 797.5).

Blood glucose levels (FIG. 9B) in all three groups began to increase by 5 minutes post-dosing indicating nasal congestion, with or without concomitant administration of a nasal decongestant, did not have an effect on the onset the glycemic response. Overall, the glucose profile after administration of intranasal glucagon was comparable regardless of the presence of common cold or the administration of a decongestant in subjects with common cold.

The results of this study indicate the PK or PD of the powder administered intranasally is not significantly affected by nasal congestion associated with common cold, with or without concomitant administration of a nasal decongestant. This is very important because people with diabetes who take insulin are at risk of experiencing severe hypoglycemia at any time, including when suffering from allergies or a common cold. As such, an intranasal glucagon intended for treatment of severe hypoglycemia must also be effective in the presence of nasal congestion.

Example 12

Biocompatibility, safety and tolerability of the compositions of this invention were evaluated in a series of studies conducted in rats, dogs and rabbits. Subchronic and acute toxicity were evaluated. Table 8 shows findings from these studies. The studies show that the compositions of the current invention are well tolerated with no adverse effects.

TABLE 8

Subchronic and acute toxicity studies in rats, dogs and rabbits.

| Study Type | Species | Test Articles & Dosage | Key findings |
| --- | --- | --- | --- |
| 28 day subchronic toxicology | Dog | Saline, placebo powder, AMG504-1 at 2 and 4 mg/dog/day for 28 days | Other than transient (i.e., <30 seconds) snorting and salivation immediately post-dosing, no adverse clinical signs. No adverse gross necropsy findings or treatment-related effects on BW, food consumption, clinical chemistry, hematology, EKG or organ weights. Minimal to moderate fully reversible atrophy/degeneration of the olfactory epithelium. No microscopic test article-related findings upon histological examination of all tissues. |
| 28 day subchronic toxicology | Rat | Saline, placebo liquid, AMG504-1 ingredients in solution at 0.1 and 0.2 mg/rat/day for 28 days | No adverse clinical signs or gross necropsy findings. No treatment-related effects on BW, food consumption, clinical chemistry, hematology, EKG or organ weights. Minimal to moderate fully reversible erosion/ulceration of olfactory epithelium in high dose group. No microscopic test article-related findings upon histological examination of all tissues. |
| Acute toxicology | Rat | Air placebo control, AMG504-1 at 0.5 mg intratracheally | No adverse clinical, macroscopic or microscopic findings |
| Acute toxicology | Rabbit | 30 mg drug product administered directly in eye | Well tolerated, with minimal ocular irritation limited to slight erythema and edema localized to the conjunctiva and palpebral membrane. |

REFERENCES (ALL OF WHICH ARE INCORPORATED HEREIN BY REFERENCE)

C. Boesch, L. R. Brown, and K. Wuethrich. Physicochemical characterization of glucagon-containing lipid micelles. Biochim. Biophys. Acta 603: 298-312, 1980.
L. R. Brown, C. Boesch and K. Wuthrich. Location and orientation relative to the micelle surface for glucagon in mixed micelles with dodecylphosphocholine: EPR and NMR studies. Biochim. Biophys. Acta 642: 296, 1981
S. Carstens and M. Sprehn. Prehospital treatment of severe hypoglycaemia: A comparision of intramuscular glucagon and intravenous glucose. Prehospital and Disaster Medicine 13: 44-50, 1998
Chabenne et al., MOLECULAR METABOLISM 3 (2014) 293-300.
P. E. Cryer. Hypoglycaemia: The limiting factor in the glycaemic management of type I and type II diabetes. Diabetologia 45: 937-948, 2002.
P. E. Cryer. Hypoglycemia in diabetes. American Diabetes Association. 2009.
R. Curran. A milestone change in practice. A call for widespread application of intranasal medication delivery in the prehospital environment. www.emsworld.com. 2007

Deary. Symptoms of hypoglycaemia and effects on mental performance and emotions. In: Hypoglycaemia in Clinical Diabetes. Second Edition. Eds. B. M. Frier and M. Fisher. 2007.

H. Dodziuk. Cyclodextrins and their complexes. Wiley-VCH Verlag, Berlin, 2006.

K. Endo, S. Amikawa, A. Matsumoto, N. Sahashi and S. Onoue. Erythritol-based dry powder of glucagon for pulmonary administration. Int. J. Pharm. 290: 63-71, 2005.

R. M. Epand and J. M. Sturtevant. A calorimetric study of peptide-phospholipid interactions: The glucagon-dimyristoylphosphatidylcholine complex. Biochemistry 20: 4603-4606, 1981.

R. M. Epand and J. M. Sturtevant. Studies on the interaction of glucagon with phospholipids. Biophys. J. 37: 163-164, 1982.

J. Filipovic-Grcic and A. Hafner. Nasal powder drug delivery. Chapter 5.7, p. 651-681, In: *Pharmaceutical Manufacturing Handbook: Production and Processes*, Edited by S. C. Gad, Wiley-Interscience, New York, 2008, pp. 1384.

L. Freychet, N. Desplanque, P. Zirinis, S. W. Rizkalla, A. Basdevant, G. Tchobroutsky and G. Slama. Effect of intranasal glucagon on blood glucose levels in healthy subjects and hypoglycaemic patients with insulin-dependent diabetes. The Lancet. pp. 1364-1366, Jun. 18, 1988

Glucagon for injection (rDNA origin). Package Insert. Eli Lilly & Co. 2005.

G. Harris, A. Diment, M. Sulway and M. Wilkinson. Glucagon administration—underevaluated and undertaught. Practical Diabetes Int. 18: 22-25, 2001.

M. A. Howell and H. R. Guly. A comparison of glucagon and glucose in prehospital hypoglycaemia. J. Accid. Emerg. Med. 14: 30-32 (1997).

A. Hvidberg, R. Djurup and J. Hilsted. Glucose recovery after intranasal glucagon during hypoglycaemia in man. Eur. J. Clin. Pharmacol. 46: 15-17, 1994.

IDF Diabetes Atlas, International Diabetes Foundation, Fourth Edition, 2009.

ISMP Canada Safety Bulletin. Administration of product-specific diluent without medication. Institute for Safe Medication Practices Canada. 10(7): 1-3, 2010.

K. K. Jain. Drug Delivery Systems. Methods in Molecular Biology. Vol. 437. pp. 8-9, Humana Press, Totowa, N.J., 2008.

S. Jorgensen, A. R. Sorensen, L. L. Kimer and N. Mygind. A powdery formulation of glucagon for nasal delivery—a phase 1 study. Diabetes 40 [Suppl A]:2190, 1991

N. C. Kaarsholm. Stabilized aqueous glucagon solutions comprising detergents. Patent numbers WO9947160, EP19990906095, 1999.

N. C. Kaarsholm. Stabilized aqueous peptide solutions. U.S. Pat. No. 6,384,016, 1999a.

D. Lichtenberg. Liposomes as a model for solubilization and reconstitution of membranes. Chapter 13. pp. 199-218. In: Handbook of nonmedical applications of liposomes. Models for biological phenomena. Vol II, Ed. Y. Barelholz and D. D. Lasic, CRC Press, Boca Raton Fla. pp. 379, 1996

Marsh, D. Handbook of lipid bilayers. CRC Press, Boca Raton, Fla., 387 pp., 1990.

L. Matilainen, K. L. Larsen, R. Wimmer, P. Keski-Rahkonen, S. Auriola, T. Jarvinen and P. Jarho. The effect of cyclodextrins on chemical and physical stability of glucagon and characterization of glucagon/gamma-CD inclusion complexes. J. Pharm. Sci. 97: 2720-2729, 2008.

L. Matilainen, S. L. Maunu, J. Pajander, S. Auriola. I. Laaskelainen, K. L. Larsen, T. Jarvinen and P. Jarho. The stability and dissolution properties of solid glucagon/gamma-cyclodextrin powder. Eur. J. Pharm. Sci. 36: 412-420, 2009.

S. Onoue, K. Yamamoto, Y. Kawabata, M. Hirose, T. Mizumoto and S. Yamada. Novel dry powder inhaler formulation of glucagon with addition of citric acid for enhanced pulmonary delivery. Int. J. Pharm. 382: 144-150, 2009.

R. P. Oomen and H. Kaplan. Binding of glucagon to lipid bilayers. Biochem. Cell Biol. 68: 284-291, 1990.

J. E. Sondergaard Pederson. The nature of amyloid-like glucagon fibrils. J. Diab. Science Tech. 4: 1357-1367. 2010.

A. E. Pontiroli, M. Alberetto and G. Pozza. British Medical Journal. 287: 462-463, 1983.

A. E. Pontiroli, M. Alberetto, A. Calderara, E. Pajetta and G. Pozza. Nasal administration of glucagon and human calcitonin to healthy subjects: a comparison of powders and spray solutions and of different enhancing agents. Eur. J. Clin. Pharmacol. 37: 427-430, 1989.

A. M. Rosenfalck, I. Bendtson, S. Jorgensen and C. Binder. Nasal glucagon in the treatment of hypoglycaemia in type 1 (insulin-dependent) diabetic patients. Diabetes Research and Clinical Practice. 17: 43-50, 1992.

F. M. Sakr. Nasal administration of glucagon combined with dimethyl-ß-cyclodextrin: comparison of pharmacokinetics and pharmacodynamics of spray and powder formulations. Int. J. Pharmaceutics 132: 189-194, 1996.

Sibley et al. Prehosp. Emer. Care. Vol. 17: 98-102, 2013.

E. Stenninger and J. Aman. Intranasal glucagon treatment relieves hypoglycaemia in children with type 1 (insulin-dependent) diabetes mellitus. Diabetologia. 36: 931-935, 1993.

D. Teshima, A. Yamauchi, K. Makino, Y. Kataoka, Y. Arita, H. Nawata and R. Oishi. Nasal glucagon delivery using microcrystalline cellulose in healthy volunteers. Int. J. Pharm. 233: 61-66, 2002.

D. P. Tieleman, D. van der Spoel and H. J. C. Berendsen. Molecular dynamics simulations of dodecyl phosphocholine micelles at three different aggregate sizes: micellar structure and lipid chain relaxation. J. Phys. Chem. B 104:6380-6388, 2000

O. Yanai, D. Pilpel, I. Harman, E. Elitzur-Leiberman and M. Philip. IDDM patients' opinions on the use of Glucagon Emergency Kit in severe episodes of hypoglycaemia. Practical Diabetes Int. 14: 40-42, 1997.

Sequences (SEQ ID NO: 1)
His-Ser-Gln-Gly-Thr-Phe-Thr-Ser-Asp-Tyr-Ser-Lys-
Tyr-Leu-Asp-Ser-Arg-Arg-Ala-Gln-Asp-Phe-Val-Gln-
Trp-Leu-Met-Asn-Thr

We claim:

1. A powder composition comprising glucagon (SEQ ID NO: 1), a phospholipid, and ß-cyclodextrin, wherein the ratio of glucagon to phospholipid to ß-cyclodextrin is 1:1:8 by weight.

2. The powder composition of claim 1, wherein the phospholipid is at least one member selected from the group consisting of dodecylphosphocholine, didecylphosphatidylcholine, lysolauroylphosphatidylcholine, dioctanoylphosphatidylcholine, dilauroylphosphatidylglycerol or mixtures thereof.

3. The powder composition of claim 2, wherein the phospholipid is dodecylphosphocholine.

4. The powder composition of claim 2, wherein the phospholipid is didecylphosphatidylcholine.

5. The powder composition of claim 2, wherein the phospholipid is lysolauroylphosphatidylcholine.

6. The powder composition of claim 2, wherein the phospholipid is dioctanoylphosphatidylcholine.

7. The powder composition of claim 2, wherein the phospholipid is dilauroylphosphatidylglycerol.

8. A powder composition consisting of glucagon (SEQ ID NO: 1), dodecylphosphocholine, and ß-cyclodextrin, wherein the ratio of glucagon to dodecylphosphocholine to ß-cyclodextrin is 1:1:8 by weight.

9. The powder composition according to claim 1, further comprising sodium citrate or citric acid.

10. The powder composition according to claim 9, wherein the amount of sodium citrate or citric acid is up to 10 percent by weight of the overall weight of the composition.

11. The powder composition according to claim 1, further comprising water.

12. The powder composition according to claim 11 wherein the water content of the composition is below 5 percent by weight of the overall weight of the composition.

13. A nasal applicator for a powder formulation, said applicator including a powder formulation reservoir, and a powder formulation contained within the reservoir, wherein the powder formulation is a composition in accordance with claim 1.

14. A method for preparing a powder formulation of claim 1, wherein at least a portion of the powder is present in a phase characterized by an XRPD mesopeak as determined by x-ray powder diffraction, said method comprising the steps of
   a. forming a first solution of the glucagon (SEQ ID NO. 1) and the phospholipid in an aqueous carrier, wherein the phospholipid is present in a concentration greater than or equal to the critical micelle concentration;
   b. adding the ß-cyclodextrin to the first mixture to form a second mixture;
   c. drying the second mixture to form a solid formulation; and
   d. processing the solid formulation to produce a uniform powder, said uniform powder including at least a portion of the powder in a phase characterized by an XRPD mesopeak.

15. A method for preparing a powder formulation of claim 1, said method comprising the steps of
   a. forming a first solution of the glucagon (SEQ ID NO. 1) and the phospholipid in an aqueous carrier, wherein the phospholipid is present in a concentration greater than or equal to the critical micelle concentration;
   b. adding the ß-cyclodextrin to the first mixture to form a second mixture;
   c. drying the second mixture to form a solid formulation; and
   d. processing the solid formulation to produce a uniform powder.

16. The method of claim 14, wherein the drying of the second mixture is carried out by freeze drying or spray drying the second mixture.

17. The method of claim 15, wherein the drying of the second mixture is carried out by freeze drying or spray drying the second mixture.

18. A method for treating hypoglycemia in an individual suffering from hypoglycemia comprising administering to the individual a composition in accordance with claim 1, wherein the composition is administered in a therapeutically effective amount as a powder to the nasal mucosa of the individual.

19. The method of claim 18, wherein the powder formulation is administered to only one nostril of the individual.

* * * * *

UNITED STATES PATENT AND TRADEMARK OFFICE
CERTIFICATE OF CORRECTION

PATENT NO. : 10,213,487 B2
APPLICATION NO. : 15/545332
DATED : February 26, 2019
INVENTOR(S) : Sankaram Mantripragada et al.

It is certified that error appears in the above-identified patent and that said Letters Patent is hereby corrected as shown below:

In the Claims

In Claim 14, at Column 27, Line 59, the phrase "powder formulation" should be changed to "powder composition."

In Claim 15, at Column 28, Line 33, the phrase "powder formulation" should be changed to "powder composition."

Signed and Sealed this
Eighteenth Day of June, 2019

Andrei Iancu
*Director of the United States Patent and Trademark Office*

SEQUENCE LISTING

<160> NUMBER OF SEQ ID NOS: 1

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25